(12) United States Patent
Han et al.

(10) Patent No.: US 8,783,466 B2
(45) Date of Patent: Jul. 22, 2014

(54) CONTINUOUS BIOMOLECULE SEPARATION IN A NANOFILTER

(75) Inventors: Jongyoon Han, Bedford, MA (US); Jianping Fu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 25 days.

(21) Appl. No.: 13/005,840

(22) Filed: Jan. 13, 2011

(65) Prior Publication Data

US 2011/0114486 A1    May 19, 2011

Related U.S. Application Data

(63) Continuation of application No. 11/543,252, filed on Oct. 5, 2006, now abandoned.

(60) Provisional application No. 60/723,926, filed on Oct. 6, 2005.

(51) Int. Cl.

| | |
|---|---|
| *B03B 5/00* | (2006.01) |
| *B01D 61/02* | (2006.01) |
| *B82Y 30/00* | (2011.01) |
| *B01L 3/00* | (2006.01) |
| *G01N 15/02* | (2006.01) |

(52) U.S. Cl.
CPC ........... *B82Y 30/00* (2013.01); *B01L 2400/086* (2013.01); *B01L 2400/0415* (2013.01); *B01D 61/027* (2013.01); *B01L 2200/0647* (2013.01); *B01L 2400/0487* (2013.01); *B01L 3/502761* (2013.01); *B01L 2300/0896* (2013.01); *B01L 3/502746* (2013.01); *G01N 2015/0288* (2013.01); *B01L 2300/0864* (2013.01)
USPC ........... 209/155; 204/450; 204/600; 209/156; 422/502

(58) Field of Classification Search
USPC .......... 209/155, 156; 204/451, 600, 601, 450; 435/283.1; 422/502
See application file for complete search history.

(56) References Cited

U.S. PATENT DOCUMENTS

| | | |
|---|---|---|
| 4,693,804 A | 9/1987 | Serwer |
| 5,011,586 A | 4/1991 | Finney et al. |
| 5,427,663 A | 6/1995 | Austin et al. |
| 6,027,623 A | 2/2000 | Ohkawa |
| 6,110,339 A | 8/2000 | Yager |
| 6,261,430 B1 | 7/2001 | Yager et al. |
| 6,280,590 B1 | 8/2001 | Cheng et al. |
| 6,881,317 B2 | 4/2005 | Huang et al. |
| 6,893,879 B2 | 5/2005 | Petersen et al. |
| 7,150,812 B2 | 12/2006 | Huang et al. |
| 2006/0252087 A1 | 11/2006 | Tang et al. |

OTHER PUBLICATIONS

Austin, "Ratchets, the problems with boundary conditions in insulating fluids" Appln. Phys. A 75, pp. 279-284 (2002).

(Continued)

*Primary Examiner* — Joseph C Rodriguez
*Assistant Examiner* — Kalyanavenkateshware Kumar
(74) *Attorney, Agent, or Firm* — Gesmer Updegrove LLP

(57) ABSTRACT

This invention provides a method and an apparatus for quickly continuously fractionating biomolecules, such as DNAs, proteins and carbohydrates by taking advantage of differential bidirectional transport of biomolecules with varying physico-chemical characteristics, for example size, charge, hydrophobicity, or combinations thereof, through periodic arrays of microfabricated nanofilters. The passage of biomolecules through the nanofilter is a function of both steric and electrostatic interactions between charged macromolecules and charged nanofilter walls, Continuous-flow separation through the devices of this invention are applicable for molecules varying in terms of any molecular properties (e.g., size, charge density or hydrophobicity) that can lead to differential transport across the nanofilters.

35 Claims, 10 Drawing Sheets

(56) References Cited

OTHER PUBLICATIONS

Baba et al., "DNA size separation using artificially nanostructured matrimatrix" Appl. Phys. Lett. 83, pp. 1468-1470 (2003).

Chou et al., "Sorting by diffusion: an asymmetric obstacle course for continuous molecular separation" Proc. natl. Acad. Sci., USA, 96, pp. 13762-13765 (1999).

Han et al., "Separation of long DNA molecules in a microfabricated entropic trap array" Science 288, pp. 1026-1029 (2000).

Han et al., "Entropic trapping and escape of long DNA molecules at submicron size constriction" Phys. Rev. Lett. 83, pp. 1688-1691 (1999).

Huang et al., "Role of Molecular size in rachet fractionation" Phys. Rev. Lett. 89 art No. 178301 (2002).

Huang et al., "Continuous particle separation through deterministic lateral displacement" Science 304, pp. 987-990 (2004).

Kaji et al., "Separation of long DNA molecules by quartz nanopillar chips under a direct current electric field" Anal. Chem. 76, pp. 15-22 (2004).

Liu et al., "Entropic trapping of macromolecules by mesoscopic periodic voids in polymer hydrogel" Nature 397, pp. 141-144 (1999).

Nykypanchuk et al., "Brownian motion of DNA confined within a two-dimensional array" Science 297, pp. 987-990 (2002).

Turner et al., "Monolithic nanofluid sieving structures for DNA manipulation" J. Vac. Sci. Technol. B 16, pp. 3538-3840 (1998).

Van Oudenaarden et al., 'Brownian ratchets: molecular separation in lipid bilayers supported on patterned arrays Science 285, pp. 1046-1048 (1999).

Volkmuth et al., "DNA elecrophoresis in microlithographic arrays" Nature 358, pp. 600-602 (1992).

Fu et al., "Nanofilter array chip for fast gel-free biomolecule separation" Appl. Phys. Lett. 89, art No. 263902 (2005).

Fu et al., "Molecular sieving in periodic free-energy landscapes created by patterned nanofilter arrays" Phys. Rev. Lett. 97, art. No. 018103 (2006).

Giddings et al.,"Statistical theory for the equilibrium distribution of rigid molecules in inert porous networks. Exclusion chromatography", J. Phys. Chem. 72, pp. 4397-4408 (1968).

Huang et al., "Generation of large-area tunable uniform electric fields in microfluid arrays for rapid DNA separation", Tech. Dig. Int. Elect. Dev. Mtg. pages IEEE, 363-366 (2001).

Schoch et al., "pH-cotrolled diffusion of proteins with different pI values across a nanochannel on a chip" Nano Lett. 6, pp. 543-547 (2006).

Tessier et al., "Electrophoretic separation of long polyelectrolytes in submolecular-size constrictions: a Monte Carlo study" Macromolecules 35, pp. 4791-4800 (2002).

Cao et al., "Fabrication of 10 nm enclosed nanofluidic channels" Appl. Phys. Letters 81, pp. 174-176 (2002).

Figure 6a-f

CONTINUOUS BIOMOLECULE SEPARATION IN A NANOFILTER

PRIORITY INFORMATION

The present application is a continuation of U.S. application Ser. No. 11/543,252, filed on Oct. 5, 2006, that claims priority to U.S. Provisional Application No. 60/723,926, filed on Oct. 6, 2005, both of which are incorporated herein by reference in their entireties.

GOVERNMENT INTEREST STATEMENT

This invention was made with government support under Grant No. CTS0347348 awarded by the National Science Foundation. The government has certain rights in this invention.

FIELD OF THE INVENTION

This invention is directed to sorting devices comprising nanoseparation matrices, an apparatus comprising the same, and methods of use thereof for high throughput molecular separations.

BACKGROUND OF THE INVENTION

In systems biology, and in the application of biomarker detection and biosensing, the separation and identification of many proteins, small molecules, and carbohydrates from a cell or from complex biological samples, is necessary. Often, one needs to profile the concentrations of many different biomarkers, cytokines and other signaling molecules contained in serum, to determine or diagnose the current progress of a disease. However, these biomarkers (typically smaller than 30 kD) are present at relatively low concentrations (pM~nM), while majority proteins (albumin and globulins, typically larger than 40 kD) are present at much higher concentrations (μM~mM), which critically limits the detection of the smaller biomarkers.

Pre-fractionation and separation could eliminate background molecules to enhance the detection ability of the signaling molecules, but none of the conventional separation techniques is appropriate for this task. Gel electrophoresis is routinely used for separating proteins based on size, but they are generally slow and hard to automate, and require bulky equipment. Capillary Electrophoresis (CE) with a liquid sieving matrix is currently the fastest size-based separation technique for protein, but polymeric sieving matrix can interfere with downstream separation and detection processes, which limits the automation of the entire sample preparation process. While microfluidic biomolecule separation systems hold much promise for miniaturizing and automating biomolecule analysis processes, most adopt the same gel sieve material in their separation, with all inherent limitations of the conventional techniques.

Micro/nanofluidic molecular sieving structures fabricated with semiconductor technology have been used to separate biomolecules as well, with much greater speed than their conventional counterparts, though to date the systems have only successfully been used for large biomolecule separation such as viral DNA based on size.

Thus, a high-throughput biomolecular sorter, which can be automated, and can be readily incorporated into downstream analysis modules is desirable, yet is currently not readily accomplished.

SUMMARY OF THE INVENTION

In one embodiment, this invention provides a biomolecular sorter comprising:
a) a substrate;
b) a plurality of obstacles arranged at regular intervals in a plurality of rows, columns or combinations thereof on a surface of said substrate;
c) a sample inlet to said sorter;
d) at least a first conduit for applying an electrostatic force field or hydrodynamic force field parallel in direction to said rows; and
e) at least a second conduit for applying an electrostatic force field or hydrodynamic force field parallel in direction to said columns, and perpendicular in direction to said rows;
wherein said obstacles are so arranged as to form gaps between said obstacles, with horizontal gaps being of a width less than vertical gaps between said obstacles.

According to this aspect of the invention, and in one embodiment, the horizontal gaps are from about 10-5000 nm, and in another embodiment, the vertical gaps are from about 0.1-10 μm. In another embodiment, the obstacles in the rows are laterally shifted with respect to each row.

In one embodiment, the gaps form channels for fluid conductance, when fluid is introduced in said sorter. In another embodiment, microfluidic channels are in fluid communication with the channels. In one embodiment, channels comprise sample loading ports, and in another embodiment, the channels comprise sample collection ports.

In another embodiment, the microfluidic channels are in fluid communication with a reservoir. In one embodiment, voltage is applied to said reservoir, which in one embodiment is less than 1000 V. In another embodiment, pressure is applied to said reservoir.

In one embodiment, the electrostatic force field or hydrodynamic force field is applied in pulse-field operation mode, or in another embodiment, in continuous-field operation mode.

In another embodiment, this invention provides a method of sorting a fluid mixture comprising a plurality of biopolymers, which vary in terms of the physico-chemical characteristics of each of said plurality of biopolymers, said method comprising the steps of:
a) loading a fluid mixture comprising a plurality of biopolymers in a biomolecular sorter comprising:
  i. a substrate;
  ii. a plurality of obstacles arranged at regular intervals in a plurality of rows, columns or combinations thereof on a surface of said substrate, wherein said obstacles are so arranged as to form gaps between said obstacles, with horizontal gaps being of a width less than vertical gaps between said obstacles, and said gaps form channels for fluid conductance, when fluid is introduced in said sorter;
  iii. a sample inlet to said sorter;
  iv. microfluidic channels in fluid communication with said channels;
  v. sample collection ports in fluid communication with said channels;
  vi. at least a first conduit for applying an electrostatic force field or hydrodynamic force field parallel in direction to said rows;
  vii. at least a second conduit for applying an electrostatic force field or hydrodynamic force field parallel in direction to said columns, and perpendicular in direction to said rows; and b) applying said electrostatic force field or hydrodynamic force field parallel in direction to said rows, and said electrostatic force field or hydrodynamic force field parallel in direction to said columns, and perpendicular in direction to said rows, whereby applying said force fields allows for size-based separation of said plurality of biopolymers through said channels; and c) collecting separated biopolymers obtained in (b) from said sample collection ports.

According to this aspect of the invention, and in one embodiment, the fluid mixture comprises a cell lysate or tissue homogenate, or in another embodiment, the fluid mixture comprises a large sample of deoxyribonucleic acids (DNA), proteins, or a combination thereof. In another embodiment, the fluid mixture comprises a buffered solution. In another embodiment, the method further comprises the step of sorting a sample of said mixture two or more times, wherein the pH or ionic strength of said buffered solution is varied at the time of said sorting. In another embodiment, the physico-chemical characteristics comprise size, charge, hydrophobicity, hydrophilicity, or a combination thereof.

In one embodiment, the electrostatic force field parallel in direction to the rows provides an electroosmotic driving force for the fluid. According to this aspect of the invention and in one embodiment, the fluid has an ionic strength of about 1-300 mM.

In one embodiment, the sorting is size-based. According to this aspect of the invention and in one embodiment, greater separation of the biopolymers is achieved with increasing voltage. In one embodiment, the voltage applied is at least 60V, or in another embodiment, at least 70V, or in another embodiment, at least 100V, or in another embodiment, at least 150V.

In one embodiment, the fluid has an ionic strength of at least 100 mM. In one embodiment, the fluid has an ionic strength of at least 125 mM, or in another embodiment, at least 150 mM.

In one embodiment, the sorting is charge-based. According to this aspect of the invention and in one embodiment, greater resolution of said biopolymers is achieved when the applied voltage is greater than 40 V.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4 has the same band assignment as FIG. 3. In all the experiments, the horizontal and vertical electric fields are 200V/cm (Eh) and 300 V/cm (Ev), respectively. Different durations are applied in different tests: (A) ΔTh/ΔTv=200 ms/200 ms; (B) ΔTh/ΔTv=200 ms/1000 ms; (C) ΔTh/ΔTv=100 ms/2000 ms;

for d, $E_x$=35 V/cm, 4=12.5 V/cm; for e, $E_x$=35 V/cm, $E_y$=50 V/cm; for f, $E_x$=35 V/cm, $E_y$=75 V/cm. Band assignment: (1) 50-bp; (2) 150-bp; (3) 300-bp; (4) 500-bp; (5) 766-bp. Fluorescence intensity profiles (of arbitrary units) were measured at the ANA bottom edge. The bars underneath the peaks are centered at the means and label the stream widths (±s.d.).

Figure 6G:
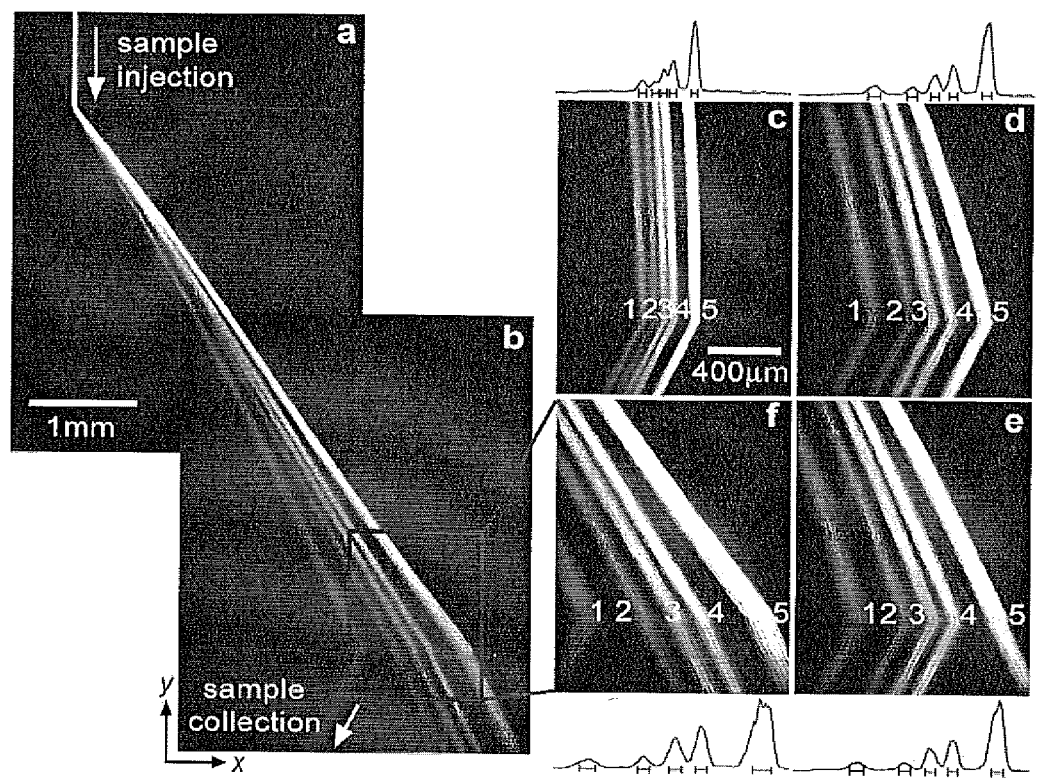
Figure 6G:
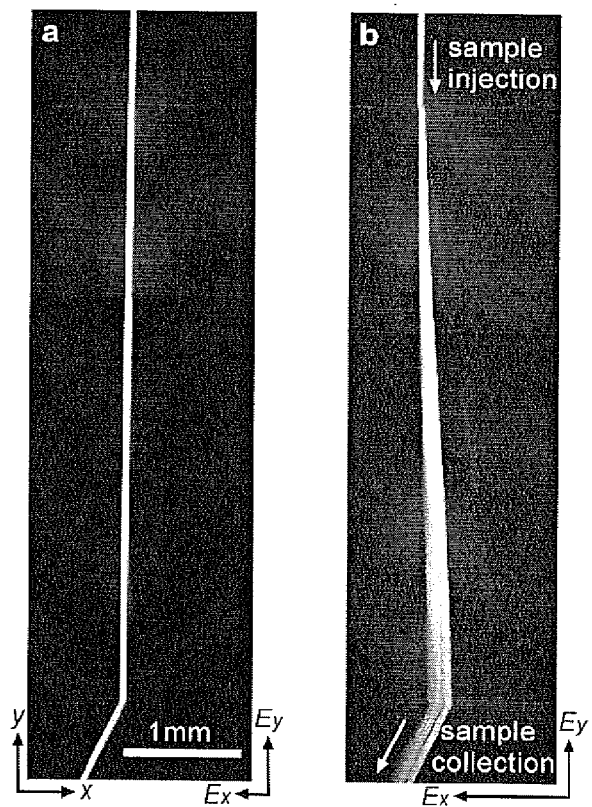

FIG. 6 demonstrates entropic trapping of a λ DNA-Hind III digest. Fluorescent photographs show separation of the λ DNA-Hind III digest under different electric filed conditions. For a, b, f, $E_x$=185 V/cm, $E_y$=100 V/cm; for c, $E_x$=50 V/cm, $E_y$=100 V/cm; for d, $E_x$=145 V/cm, $E_y$=100 V/cm; for e, $E_x$=170 V/cm, $E_y$=100 V/cm. Band assignment: (1) 2.322-kbp; (2) 4.361-kbp; (3) 6.557-kbp; (4) 9.416-kbp; (5) 23.130-kbp. Fluorescence intensity profiles were measured at the ANA bottom edge. The bars underneath the peaks are centered at the means and label the stream widths (±s.d.). For g: Observation of the threshold horizontal field $E_{x,c}$. A composite fluorescence photograph showing confining of λ DNA-Hind III digest in the initial injection deep channels with $E_x$=15 V/cm and $E_y$=25 V/cm and composite fluorescence photograph showing DNA molecules starting to jump across the nanofilter with $E_x$=50 V/cm and $E_y$=25 V/cm.

Figure 7:
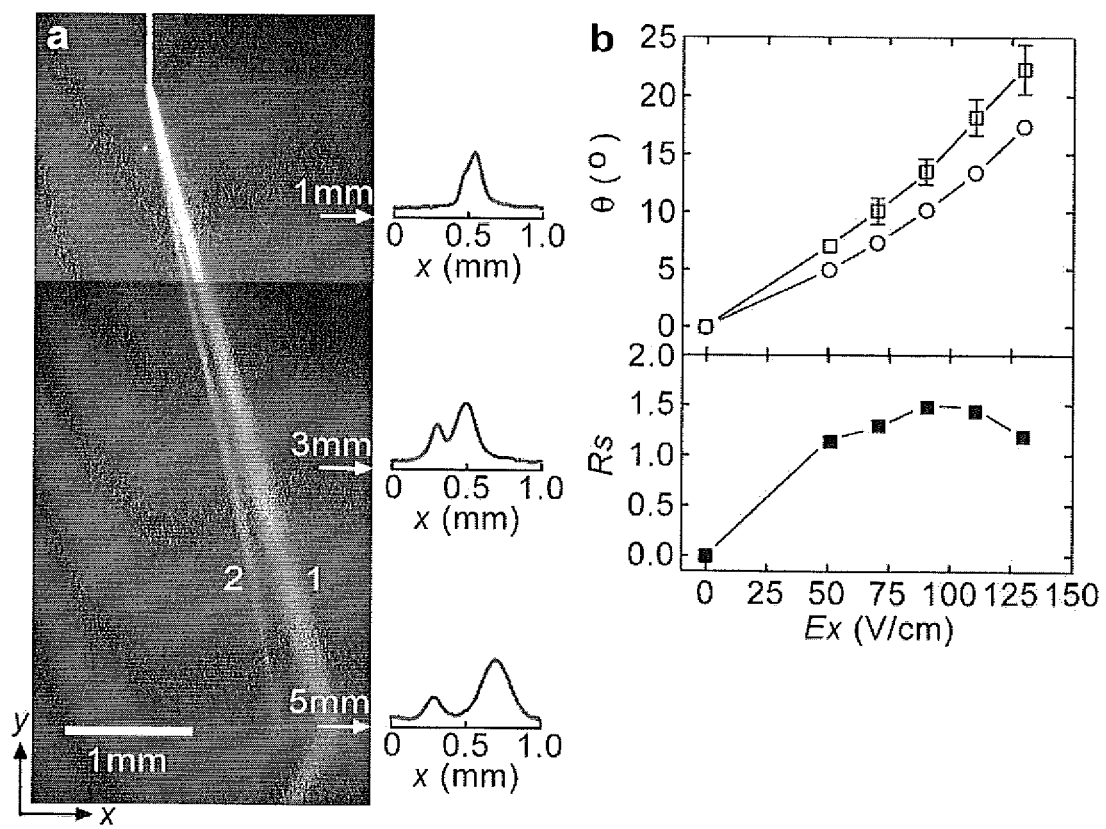

FIG. 7 demonstrates a continuous-flow separation of SDS-protein complexes through an embodiment of the device, a, Composite fluorescent photograph showing separation of cholera toxin subunit B (band 1) and β-galactosidase (band 2) with $E_x$=75 V/cm and $E_y$=50 V/cm. The three insets are electropherograms scanned at 1 mm, 3 mm, and 5 mm from the injection point, respectively. b, Measured deflection angle θ (top) of cholera toxin subunit B (~) and β-galactosidase (○) as a function of $E_x$ when $E_y$=50 V/cm. The bottom shows the corresponding separation resolutions. The ±s.d. of θ are indicated as error bars (drawn if larger than the symbol).

Figure 8:
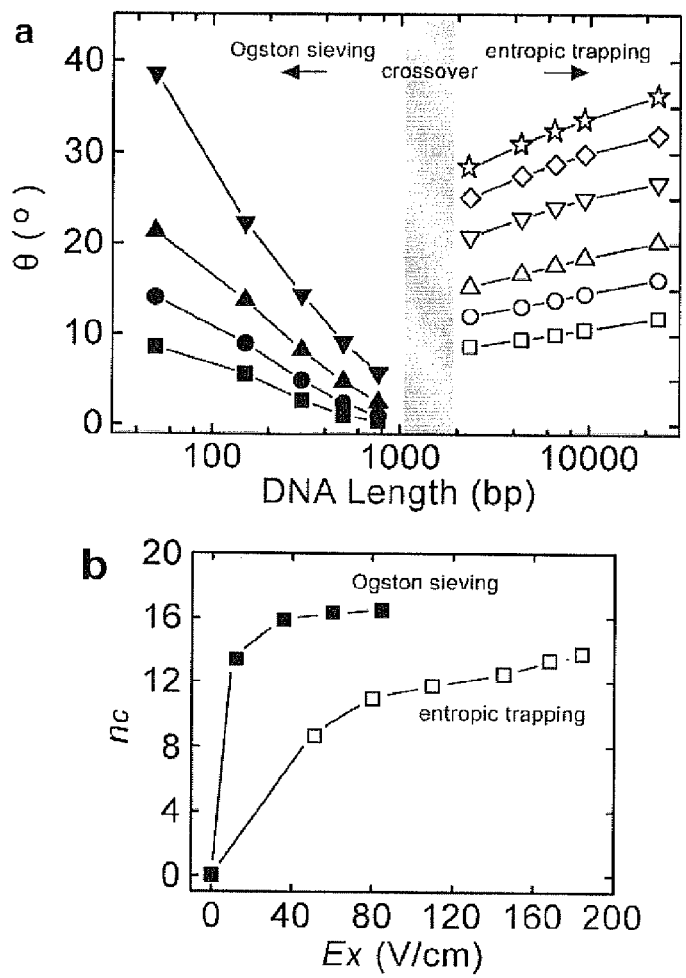

FIG. 8 demonstrates crossover of Ogston sieving and entropic trapping of DNA molecules in an embodiment of the device. a, Stream deflection angle θ as a function of DNA length. For the left side of Ogston sieving, $E_y$ is fixed at 25 V/cm, and $E_x$: 10 V/cm (■), 35 V/cm (●), 60 V/cm (▲), 85 V/cm (▼). For the right side of entropic trapping, $E_y$=100 V/cm and $E_x$: 50 V/cm (~), $E_x$: 80 V/cm (○), $E_x$: 110 V/cm (Δ), $E_x$: 145 V/cm (▽), $E_x$: 170 V/cm (◇), $E_x$: 185 V/cm (☆). The ±s.d. of θ derived from the stream half-width are all less than 1°, so statistical error bars for θ are not plotted. b, Dependence of the effective peak capacity $n_c$ on $E_x$. For Ogston sieving (solid symbols), $E_y$=25 V/cm; for entropic trapping (open symbols), $E_y$=100 V/cm.

Figure 9:
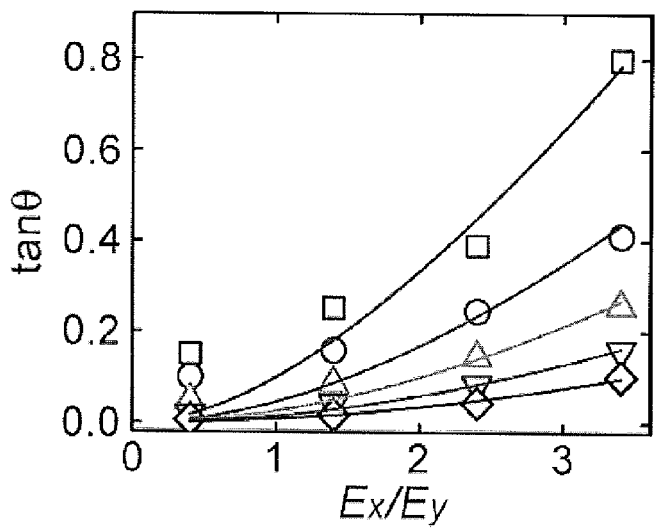

FIG. 9 demonstrates the tan θ of different streams as a function of $E_x/E_y$ at a fixed $E_y$=25 V/cm (50-bp (~), 150-bp (○), 300-bp (Δ), 500-bp (▽), 766-bp (◇)). The ±s.d. of θ derived from the stream half-width are all less than 1°, so statistical error bars for tan θ are not plotted. The colored solid lines are theoretical curves calculated from Eq. (7-2). The best fitting constant α has a mean about 177.5 and a ±s.d. about 12%.

Figure 10:
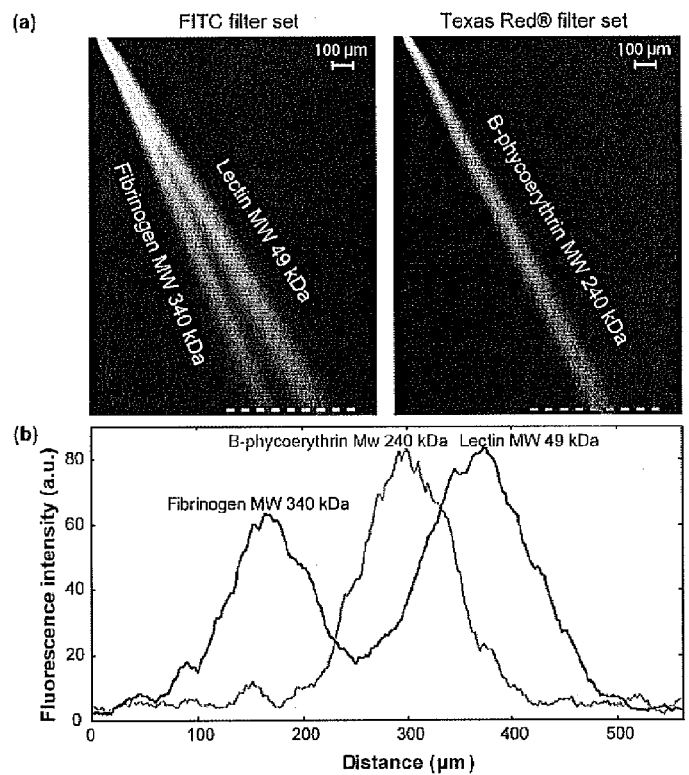

FIG. 10 demonstrates another embodiment of size-based separation of proteins. (a) Fluorescence images showing three size-based separated streams of the proteins fibrinogen (MW 340 kDa) and lectin (MW 49 kDa), which are fluorescent in the green range (FITC filter set, left) and the orange-fluorescent B-phycoerythrin with MW 240 kDa (Texas Red® filter set, right). These measurements were performed at TBE 5× with $E_x$=100 V/cm and $E_y$=50 V/cm. (b) Fluorescence intensity as a function of the distance along the dashed lines (after 30% of the total ANA length in y-direction) presented in (a), showing the separation distance between the streams. The black line was deduced from the FITC and the grey line from the Texas Red® image. A Gaussian fluorescence intensity distribution is observed for all three proteins.

Figure 11:
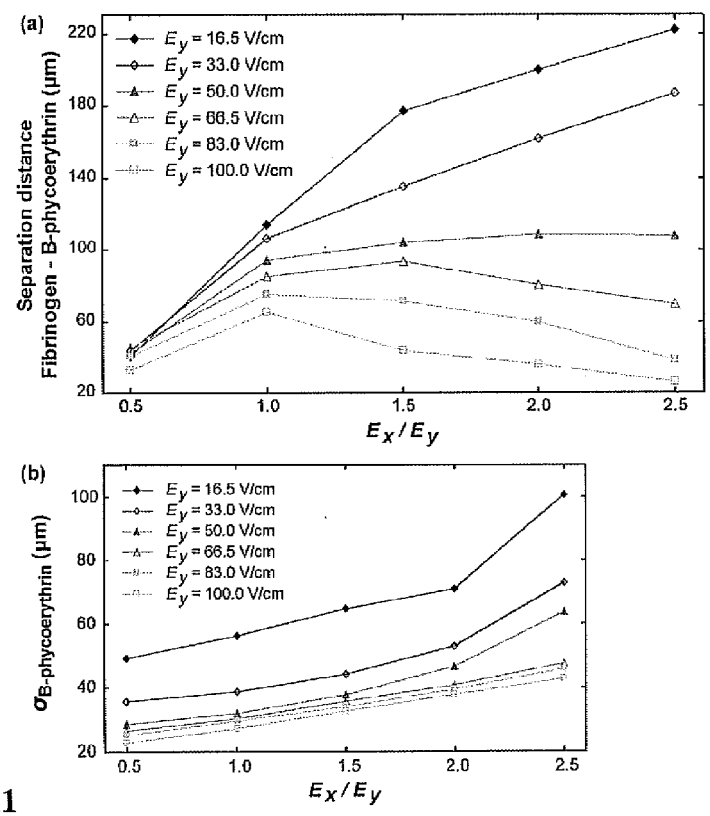

FIG. 11 demonstrates another embodiment of size-based separation of proteins and other biomolecules. (a) Separation distance between the streams of fibrinogen and B-phycoerythrin as a function of the ratio $E_x/E_y$ at TBE 5×. For a chosen $E_y$, a maximal separation distance is observed for a specific $E_x$, and the maximal separation distance increases with decreasing $E_y$, because the Peclet number decreases. (b) Standard deviation σ (half the stream width) of B-phycoerythrin versus $E_x/E_y$. Band broadening is observed with an increasing ratio of $E_x/E_y$ and with a decreasing $E_y$.

Figure 12:
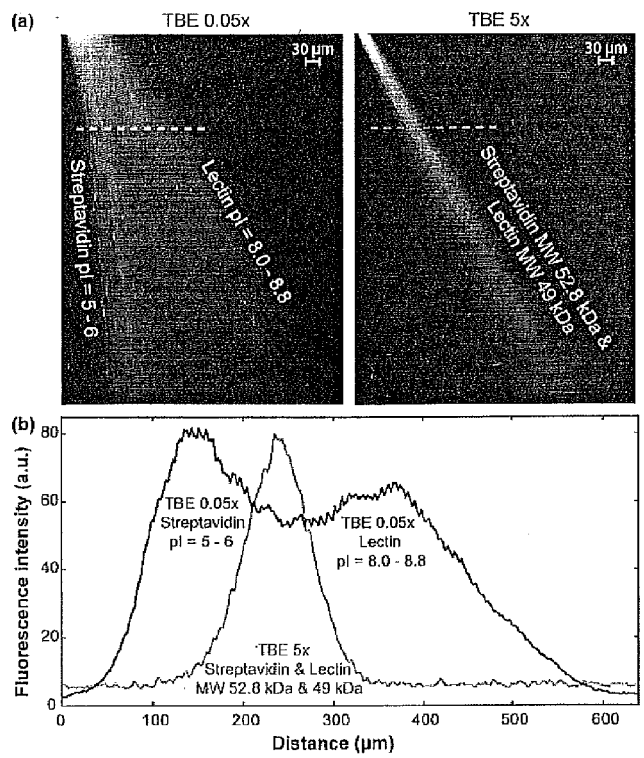

FIG. 12 demonstrates another embodiment of charge-based separation. (a) Fluorescence images presenting charge-based separation of streptavidin (pI=5-6) and lectin (pI=8.0-8.8) at TBE 0.05× in the image on the left, whereas the right image shows that the MW difference of 3.8 kDa between these two proteins can not be resolved on this ANA at TBE 5×. These results confirm the separation obtained at TBE 0.05× is charge-based. (b) Fluorescence intensity (black: TBE 0.05×, grey: TBE 5×) versus distance along the dashed lines of the images in (a), after 5% of the total length of the ANA. At TBE 0.05× the fields were $E_x$=250 V/cm and $E_y$=75 V/cm and at TBE 5×$E_x$=150 V/cm and $E_y$=75 V/cm.

Figure 13:
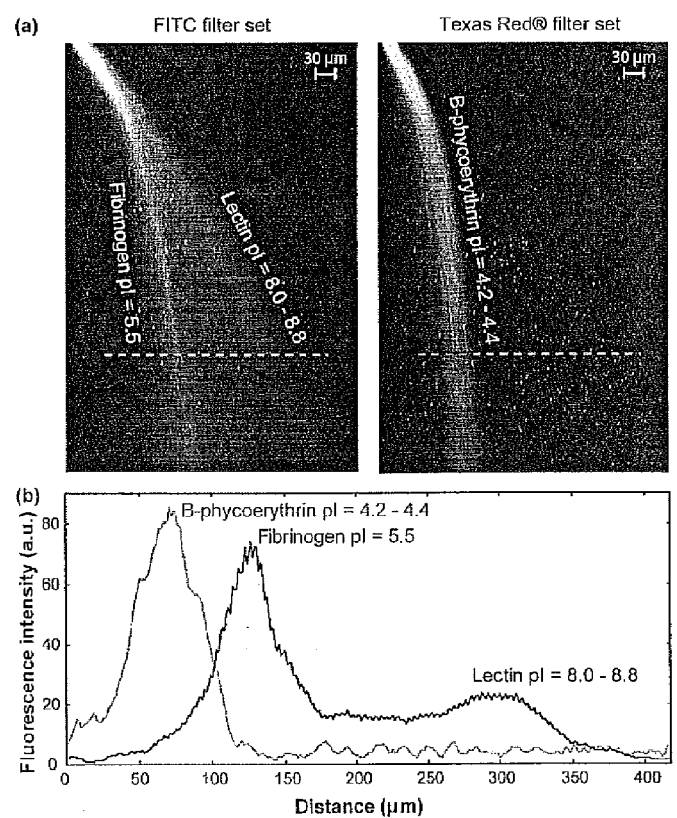

FIG. 13 demonstrates another embodiment of charged based separation of biomolecules. (a) Fluorescence images showing three charge-based separated streams corresponding to the proteins B-phycoerythrin (pI=4.2-4.4), fibrinogen (pI=5.5), and lectin (pI=8.0-8.8) observed with the FITC filter set (left) and Texas Red® filter set (right). The buffer was TBE 0.05×, pH=9.6 and the electric fields were $E_x$=250 V/cm and $E_y$=75 V/cm. (b) Fluorescence intensity (black: FITC filter set, grey: Texas Red® filter set) as a function of the distance along the dashed lines presented in (a), showing that a good separation is already obtained after 13% of the total length of the ANA. White dots are adsorbed proteins at the walls of the channels.

Figure 14:
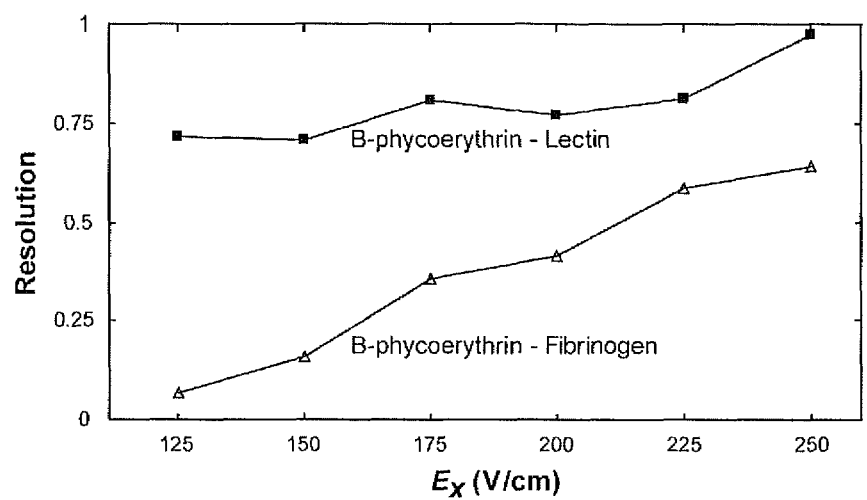

FIG. 14 demonstrates the resolution Rs of an embodiment of a charge-based separation between the streams B-phycoerythrin—lectin and B-phycoerythrin—fibrinogen as a function of EX at a fixed electric field $E_y$=75 V/cm. An increasing resolution is obtained with increasing $E_x$, because more sieving events occur as the number of nanofilters in increased. The measurements were made at TBE 0.05× and evaluated at the same y-position as done in FIG. 5 after 13% of the total length of the ANA. The x-position of the center of the stream and its width were obtained by Gaussian fits. The connecting lines are for guidance only.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment of this invention, there is provided a unique continuous-flow separation of small biomolecules such as native proteins, protein complexes and double-stranded DNA molecules (dsDNA) in a microfabricated chip, based on differential bidirectional transport of biomolecules of different sizes through periodic arrays of microfabricated nanofilters, which in one embodiment, comprises the use of a microfabricated molecular sieving chip that can size-fractionate small biomolecules without using gel sieving matrices, with a separation efficiency comparable to current means such as capillary gel electrophoresis.

In one embodiment, this invention provides a biomolecular sorter comprising:
 a) a substrate;
 b) a plurality of obstacles arranged at regular intervals in a plurality of rows, columns or combinations thereof on a surface of said substrate;
 c) a sample inlet to said sorter;
 d) at least a first conduit for applying an electrostatic force field or hydrodynamic force field parallel in direction to said rows; and
 e) at least a second conduit for applying an electrostatic force field or hydrodynamic force field parallel in direction to said columns, and perpendicular in direction to said rows;
wherein said obstacles are so arranged as to form gaps between said obstacles, with horizontal gaps being of a width less than vertical gaps between said obstacles.

In one embodiment, the substrate and/or other components of the sorter can be made from a wide variety of materials including, but not limited to, silicon, silicon dioxide, silicon nitride, glass and fused silica, gallium arsenide, indium phosphide, III-V materials, PDMS, silicone rubber, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, teflon, brass, sapphire, etc., or a combination thereof. High quality glasses such as high melting borosilicate or fused silicas may be used, in some embodiments, for their UV transmission properties when any of the sample manipulation and/or detection steps require light based technologies. In addition, as outlined herein, portions of the internal and/or external surfaces of the device may be coated with a variety of coatings as needed, to facilitate the manipulation or detection technique performed.

In one embodiment, the obstacles comprise the same materials as the substrate, or in another embodiment, are comprised of a suitable material which prevents adhesion to the obstacles. In one embodiment, the channels formed via the positioning of the obstacles may similarly comprise the same materials, or may otherwise be treated, as will be appreciated by one skilled in the art, to facilitate sorting.

In one embodiment, the invention provides for a microchip comprising the biomolecular sorter or sorters of this invention. In one embodiment, the microchip may be made of a wide variety of materials and can be configured in a large number of ways, as described and exemplified herein, in some embodiments, and other embodiments will be apparent to one of skill in the art. The composition of the substrate will depend on a variety of factors, including the techniques used to create the device, the use of the device, the composition of the sample, the molecules to be sorted, the type of analysis conducted following molecular sorting, the size of internal structures, the presence or absence of electronic components, and the technique used to move fluid, etc. In some embodiments, the devices of the invention will be sterilizable as well, in some embodiments, this is not required. In some embodiments, the devices are disposable or, in another embodiment, re-usable.

Microfluidic chips used in the methods and devices of this invention may be fabricated using a variety of techniques, including, but not limited to, hot embossing, such as described in H. Becker, et al., Sensors and Materials, 11, 297, (1999), hereby incorporated by reference, molding of elastomers, such as described in D.C. Duffy, et. al., Anal. Chem., 70, 4974, (1998), hereby incorporated by reference, injection molding, LIGA, soft lithography, silicon fabrication and related thin film processing techniques, as known in the art, photolithography and reactive ion etching techniques, as exemplified herein. In one embodiment, glass etching and diffusion bonding of fused silica substrates may be used to prepare microfluidic chips.

The arrangement of the obstacles in the sorter forms an array or rows and columns, such that the regions between obstacles in respective rows and columns are continuous, forming channels. For example, as described in FIG. 1, each row, which comprises a "thick region" (1-10) forming a channel for conveying fluid comprising molecules to be sorted, as described herein. The "thin regions" (1-20) provide steric hindrance such that larger molecules do not pass readily through these regions. In one embodiment, the regions are aligned, such that they form parallel columns, which serve as channels for conveying fluid comprising molecules to be sorted, which are small enough in size to pass through the regions. In one embodiment, the regions are staggered, such that they form staggered columns, serving as channels as described. Molecules, in turn, in a size restricted manner, transit through the thick and thin regions, partly in a direction which is in parallel to and partly in a direction which is perpendicular to the original plane of entry in the sorter.

In one embodiment, the thin regions or columns of this invention comprise nanofluidic channels, which have a width ranging from about 10-5000 nm. In one embodiment, the thick regions comprise microfluidic channels which have a width ranging from about 0.5-500 micron.

In one embodiment, the microfluidic or nanofluidic channels used in the devices and/or methods of this invention, which convey fluid, may be constructed from a material which renders it transparent or semitransparent, in order to image the solutions being sorted, or in another embodiment, to ascertain the progress of the sorting, etc. In some embodiments, the materials further have low conductivity and high chemical resistance to buffer solutions and/or mild organics. In other embodiments, the material is of a machinable or moldable polymeric material, and may comprise insulators, ceramics, metals or insulator-coated metals. In other embodiments, the channel may be constructed from a polymer material that is resistant to alkaline aqueous solutions and mild organics. In another embodiment, the channel comprises at least one surface which is transparent or semi-transparent, such that, in one embodiment, imaging of the sorter is possible.

In one embodiment, the term "minimal sorting unit" as described herein, refers to the arrangement of obstacles on the substrate, forming rows and columns, as described hereinabove, which in turn serve as channels for the conductance of the fluid mixture comprising the molecules to be sorted. In one embodiment of this invention, the sorter may further comprise microfluidic channels in fluid communication with the minimal sorting unit. In one embodiment, the latter channels are in fluid communication with a sample reservoir, or in another embodiment, buffer reservoir, or in another embodiment, inlet port, or in another embodiment, outlet port. According to this aspect of the invention, the microfluidic channels may serve as a conduit for conveying material into and out of the minimal sorting unit.

In one embodiment, a device of this invention may comprise an array comprising one or more minimal sorting units. Such arrays may be referred to herein, in other embodiments, as "anisotropic nanofilter arrays (ANAs)".

In one embodiment, the inlet may comprise an area of the chip in fluidic communication with one or more microfluidic channels, in one embodiment, and/or a sample reservoir, in another embodiment. Inlets and outlets may be fabricated in a wide variety of ways, depending upon, in one embodiment, on the substrate material utilized, and/or in another embodiment, the dimensions used. In one embodiment inlets and/or outlets are formed using conventional tubing, which prevents sample leakage, when fluid is applied to the device, under pressure. In one embodiment inlets and/or outlets are formed of a material which withstands application of voltage, even high voltage, to the device. In one embodiment, the inlet may further comprise a means of applying a constant pressure, to generate pressure-driven flow in the device.

The sorters of this invention, may be referred to in some embodiments, as a "device" or "apparatus", and will comprise at least the elements as described herein. In one embodiment, the devices of this invention comprise at least one microchannel and at least one nanochannel. In one embodiment, the terms "nanochannel" and "nanofilter" are used herein interchangeably, and refer to a size-selective construction on the sorting device, as a result of the arrangement of the obstacles and construction of the device, such that size-dependent separation is accomplished, as described. In one embodiment, the device is formed using the technology of microfabrication and nanofabrication, for formation of the respective channels.

Microfabrication technology, or microtechnology or MEMS, in one embodiment, applies the tools and processes of semiconductor fabrication to the formation of, for example, physical structures. Microfabrication technology allows one, in one embodiment, to precisely design features (e.g., reservoirs, wells, channels) with dimensions in the range of <1 mm to several centimeters on chips made, in other embodiments, of silicon, glass, or plastics. Such technology may be used to construct the microchannels of the sorter, in one embodiment.

In another embodiment, NEMS or nanotechnology is used to construct the nanochannels. In one embodiment, the nanochannels can be fabricated with nanoimprint lithography (NIL), as described in Z. N. Yu, P. Deshpande, W. Wu, J. Wang and S. Y. Chou, Appl. Phys. Lett. 77 (7), 927 (2000); S. Y. Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905 hereby incorporated herein, in their entirety, by reference. In one embodiment, the nanochannels and/or microchannels can be formed by photolithography and reactive ion etching (RIE) techniques, with nanofilter gap thickness (ds) as thin as 10 nm. In one embodiment, the formation of the device may employ nanoimprint lithography, interference lithography, self-assembled copolymer pattern transfer, spin coating, electron beam lithography, focused ion beam milling, wet-etching, plasma-enhanced chemical vapor deposition, electron beam evaporation, sputter deposition, and combinations thereof. Alternatively, other conventional methods can be used to form the nanochannels and/or microchannels.

In one embodiment, the sorter comprising nanochannels and microchannels are formed as exemplified hereinbelow in Example 1.

In one embodiment, a series of reactive ion etchings are conducted, after which nanochannels are patterned with standard lithography tools. In one embodiment, the etchings are conducted with a particular geometry, which, in another embodiment, determines the interface between the microchannels, and/or nanochannels. In one embodiment, etchings, which create the microchannels, are performed perpendicular to the plane in which etchings for the nanofilters were created.

In another embodiment, electrical insulation of the device is accomplished. In one embodiment, such insulation is accomplished via thermal oxidation of the device. In another embodiment, a surface of the device, which in another embodiment is the bottom surface, may be affixed to a substrate, such as, for example, and in one embodiment, a Pyrex wafer. In one embodiment, the wafer may be affixed using anodic bonding techniques.

In one embodiment, the fabrication may use a shaped sacrificial layer, which is sandwiched between permanent floor and ceiling layers, with the shape of the sacrificial layer defining a working gap. When the sacrificial layer is removed, the working gap becomes a fluid channel having the desired configuration. This approach, in one embodiment, allows a precise definition of the height, width and shape of interior working spaces, or fluid channels, in the structure of a fluidic device.

The sacrificial layer is formed on a substrate, shaped by a suitable lithographic process, for example, and is covered by a ceiling layer. Thereafter, the sacrificial layer may be removed with a wet chemical etch, leaving behind empty spaces between the floor and ceiling layers which form working gaps which may be used as flow channels, filters and/or reservoirs for the sorting device. In such a device, the vertical dimension, or height, of a working gap is determined by the thickness of the sacrificial layer film, which is made with, for example, chemical vapor deposition (CVD) techniques, and accordingly, this dimension can be very small.

The channels, chambers, and/or filters have dimensions on the order of microns, in the case of the microchannels and chambers/reservoirs, and nanometers, in the case of nanofilters/nanochannels. In some embodiments, structures with larger dimensions, such as on the order of millimeters, are used, and represent embodiments of this invention. In one embodiment, the width and/or length of the microfluidic chamber ranges from 100-1000 µm, and the depth of the microfluidic chamber ranges from 0.1-100 µm. In one embodiment, the width of the microchannel is between 0.1-1000 µm, or in another embodiment, between 1 and 150 µm, or in another embodiment, between 20 and 500 µm, or in another embodiment, between 25 and 750 µm, or in another embodiment, between 500 and 1000 µm. In one embodiment, the depth of the microchannel is between 0.1-50 µm, or in another embodiment, between 0.5 and 5 µm, or in another embodiment, between 5 and 15 µm, or in another embodiment, between 10 and 25 µm, or in another embodiment, between 15 and 50 µm.

In another embodiment, the width of the nanofilter is between 10 nm-500 µm, or in another embodiment, between 10 nm and 15 µm, or in another embodiment, between 20 nm and 25 µm, or in another embodiment, between 50 nm and 40 µm, or in another embodiment, between 50 nm and 50 µm. In another embodiment, the depth of the nanochannel is between 10-1000 nanometers, or in another embodiment, between 20 and 50 nanometers, or in another embodiment, between 20 and 75 nanometers, or in another embodiment, between 30 and 75 nanometers or in another embodiment, between 50 and 100 nanometers.

In one embodiment, the microchannels, which form the rows of the device and nanofilters are oriented perpendicularly, with respect to each other. In one embodiment, the term "perpendicular" or "perpendicularly" refers to an orientation of one channel being at a 90° angle with respect to the longitudinal axis of another channel, +/−5 or in another embodiment, at a 90° angle of +/−10°, or in another embodiment, at a 90° angle +/−20°.

In one embodiment, the sorter of this invention may comprise a plurality of channels, including a plurality of microchannels, or a plurality of nanochannels, or a combination thereof. In one embodiment, the phrase "a plurality of channels refers to more than two channels, or, in another embodiment, more than 5, or, in other embodiments, more than 10, 96, 100, 384, 1,000, 1,536, 10,000, 100,000 or 1,000,000 channels.

In one embodiment, the surface of the microchannel and/or nanofilter may be functionalized to reduce or enhance adsorption of species of interest to the surface of the device. In another embodiment, the surface of the microchannel and/or nanofilter has been functionalized to enhance or reduce the operation efficiency of the device.

In one embodiment, the device is further modified to contain an active agent in the microchannel. For example, and in one embodiment, the microchannel is coated with an enzyme at a region wherein molecules within the mixture will separate in a size-restricted manner, according to the methods of this invention. According to this aspect, the enzyme, such as, a protease, may come into contact with concentrated proteins, and digest them, which in another embodiment, allows for further sorting of the digested species. The digestion products may, in another embodiment, be conveyed to a peptide analysis module, downstream of the sorting device. The amino acid sequences of the digestion products may be determined and assembled to generate a sequence of the polypeptide. Prior to delivery to a peptide analysis module, the peptide may be conveyed to an interfacing module, which in turn, may perform one or more additional steps of separating, concentrating, and or focusing.

In another embodiment, the microchannel may be coated with a label, which in one embodiment is tagged, in order to identify a particular protein or peptide, or other molecule containing the recognized epitope, which may be a means of sensitive detection of a molecule in a large mixture, present at low concentration.

For example, in some embodiments, reagents may be incorporated in the buffers used in the methods and devices of this invention, to enable chemiluminescence detection. In some embodiments the method of detecting the labeled material includes, but is not limited to, optical absorbance, refractive index, fluorescence, phosphorescence, chemiluminescence, electrochemiluminescence, electrochemical detection, voltometry or conductivity. In some embodiments, detection occurs using laser-induced fluorescence, as is known in the art.

In some embodiments, the labels may include, but are not limited to, fluorescent lanthanide complexes, including those of Europium and Terbium, fluorescein, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-tetraioide, which is sold under the name YOYO-1, Cy and Alexa dyes, and others described in the 9th Edition of the Molecular Probes Handbook by Richard P. Haugland, hereby expressly incorporated by reference. Labels may be added to 'label' the desired molecule, prior to introduction into the sorters of this invention, in some embodiments, and in some embodiments the label is supplied in a microfluidic chamber. In some embodiments, the labels are attached covalently as is known in the art, or in other embodiments, via non-covalent attachment.

In some embodiments, photodiodes, confocal microscopes, CCD cameras, or photomultiplier tubes maybe used to image the labels thus incorporated, and may, in some embodiments, comprise the apparatus of the invention, representing, in some embodiments, a "lab on a chip" mechanism, as described further, as well, hereinbelow.

In one embodiment, detection is accomplished using laser-induced fluorescence, as known in the art. In some embodiments, the apparatus may further comprise a light source, detector, and other optical components to direct light onto the microfluidic chamber/chip and thereby collect fluorescent radiation thus emitted. The light source may comprise a laser light source, such as, in some embodiments, a laser diode, or in other embodiments, a violet or a red laser diode. In other embodiments, VCSELs, VECSELs, or diode-pumped solid state lasers may be similarly used. In some embodiments, a Brewster's angle laser induced fluorescence detector may used. In some embodiments, one or more beam steering mirrors may be used to direct the beam to a desired location for detection.

In one embodiment, the buffered solution is flowed through the chamber at a relatively constant flow rate, which in one embodiment ranges from about 0.5-15 µl/minute. According to this aspect of the invention, pressure applied to the device will be such as to accommodate a relatively constant flow rate, as desired, as will be understood by one skilled in the art.

In one embodiment, any of various mechanisms may be employed to manipulate, transport, and/or move fluid within the device, to convey the fluid within the microfluidic chamber, as well as into or out of the chamber. In some embodiments, pressurized fluid flow is applied from a syringe, or, in another embodiment, other pressure source, attached to, in one embodiment, an inlet of a device of this invention.

In some embodiment, a pressure stop is positioned between two or more channels in an apparatus of this invention, such that the pressure-driven flow through a first microchamber does not influence the flow through a second microchamber, in some embodiments of this invention. According to this aspect of the invention, and in one embodiment, separation may be affected by the pressure applied for the sorting of the molecules within the given microfluidic chamber.

Inlets/outlets allow access to the chambers to which they are connected for the purpose, in one embodiment, of introducing or, in another embodiment, of removing fluids from the chambers on the microfluidic chip. In one embodiment, inlets allow access to the chamber to which they are connected for the purpose of introducing fluids to the microchamber, from a sample reservoir, or in another embodiment, from a sample stored in a conventional storage means, such as a tube. In another embodiment, the outlet allows access of fluid from the microfluidic chamber which has undergone pI-based sorting, according to the methods of this invention. According to this aspect of the invention, the outlet may allow for the removal and storage of the sorted material, or in another embodiment, its conveyance to an analytical module, which in one embodiment, may be coupled thereto.

The sorting devices of this invention are so constructed that passage of biomolecules through a nanofilter is sterically hindered via an Ogston sieving process, with passage being size-dependent. An injected main stream of biomolecules separates into different streams based on molecular size, in some embodiments, as a function of the arrangement of the nanofilter arrays and applied horizontal and vertical force fields (electrostatic force field or hydrodynamic force field with pulse-field operation mode or continuous-field operation mode).

In one embodiment, the sorter comprises at least a first conduit for applying an electrostatic force field or hydrodynamic force field parallel in direction to said rows. In one embodiment, the force field is applied in parallel direction to the microchannels, which comprise the rows of the sorters, as described. The force field may be thus formed, via application of an appropriate stimulus to a reservoir, as described, which is in fluid communication with microfluidic channels, which in turn thither convey the stimulus to the microchannels of the minimal sorting unit.

In one embodiment, the microfluidic channels connecting to buffer reservoirs produce electrostatic force field or hydrodynamic force field over the minimal sorting unit by acting as electric-current injectors or fluidic flow injectors, depending upon the field applied.

The sorter will also comprise at least a second conduit for applying an electrostatic force field or hydrodynamic force field parallel in direction to the columns, and perpendicular in direction to the rows such that the two fields, as applied are perpendicularly applied, with respect to each other.

Figure 3:
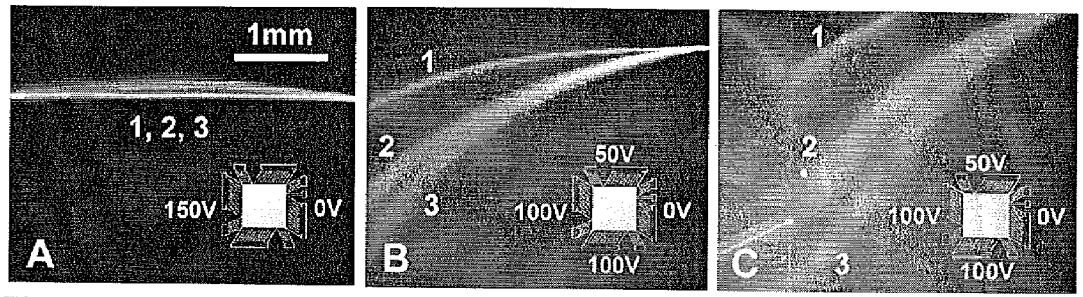
FIG. 3 shows fluorescence images of continuous field separation of SDS-protein complexes inside an embodiment of the 2-D nanofilter based matrix. Band assignment for SDS-protein complexes: (1) low density human lipoprotein (MW: 179 kDa); (2) lectin phytohemagglutinin-L (MW: 120 kDa); (3) cholera toxin subunit B (MW: 11.4 kDa). (A) No separation could be observed if only horizontal field is applied (Eh=300 V/cm). (B&C) The three SDS-proteins species are resolved with both horizontal and vertical fields applied (Eh=200 V/cm, Ev=100 V/cm). Separated molecules are collected in different channels and routed to different reservoirs.

As exemplified herein, in FIG. 3, the application of two fields, in this case electrostatic force fields were necessary for the separation of the labeled species.

In one embodiment, the electrostatic force field may be applied to the apparatus via the disposition of electrodes on a surface of the apparatus, in conjunction with its their connection to a means of applying voltage, wherein the electrodes are so positioned such that following application of voltage, an electric field is generated, which is parallel in direction to the rows comprising the microchannels of the minimal sorting unit. In another embodiment, the electrodes are so positioned such that following application of voltage, an electric field is generated, which is perpendicular in direction to the rows comprising the microchannels of the minimal sorting unit, which may also be referred to herein as a vertical force field. In some embodiments, electrodes are formed on the interior or exterior surfaces of the chip and are in electrical communication with the microfluidic channels.

According to this aspect of the invention, and in one embodiment, a power supply is coupled to the electrodes, which may further comprise a DC-to-DC converter, a voltage-controlled resistor, and a feedback circuit to control the resistor and converter to regulate the voltage of the power supply.

In some embodiments of the present invention, a power module is coupled to an external power supply. In other embodiments, the power module is powered using a portable power supply, such as batteries, solar power, wind power, nuclear power, and the like.

In some embodiments of the present invention, the voltage delivered to the device provides a field strength of up to $3.5 \times 10^4$ V/m. In one embodiment, an electric field with strength of at least 100 V/m is applied, or in another embodiment, at least 200 V/m, or in another embodiment, at least 300 V/m.

In one embodiment, the electrode metal contacts can be integrated using standard integrated circuit fabrication technology to be in contact with a reservoir, or in one embodiment, at least one microchannel, or in another embodiment, a combination thereof, and oriented as such, to establish a directional electric field, as described. Alternating current (AC), direct current (DC), or both types of fields can be applied. The electrodes can be made of almost any metal, and in one embodiment, comprise thin Al/Au metal layers deposited on defined line paths. In one embodiment, at least one end of one electrode is in contact with buffer solution in the reservoir.

In another embodiment, the sorting device may contain at least two pairs of electrodes, each providing an electric field in a different direction.

In another embodiment, at least one of the force fields may be a hydrodynamic force field. In one embodiment, both force fields are hydrodynamic force fields, or in another embodiment, one force field is hydrodynamic and the other electrostatic, or in another embodiment, both are electrostatic.

In one embodiment, a hydrodynamic force field is established via provision of a pressure driven flow, which may originate, in one embodiment, in the reservoirs, which convey fluid to the microchannels, which in turn convey the fluid to the minimal sorting unity, thus in fact acting as fluidic flow injectors. In one embodiment, the phrases "pressure-driven flow" refers to flow that is driven by a pressure source exerted on the conveyance of fluid through a segment of a channel, external to the channel segment through which such flow is driven.

Examples of pressure sources include negative and positive pressure sources or pumps external to the channel segment in question, including electrokinetic pressure pumps, which in one embodiment, are connected to a reservoir, or microchannel of this invention, which does not comprise the minimal sorting unit.

In one embodiment, reference to the term "liquid flow" may encompass any or all of the characteristics of flow of fluid or other material through a passage, conduit, channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the channel network, followed by electrokinetic movement of materials, or in another embodiment, electrokinetic movement of the liquid followed by pressure-driven flow. It is to be understood that both may be employed in the creation of a force field for either or both directions, as described herein, and may be used in order to affect the sorting efficiency or quality desired, when sorting a mixture of molecules.

The sorters of this invention and/or devices comprising the same may be used to sort a fluid mixture comprising a plurality of polymers, or in some embodiments, biopolymers, for example, peptides, nucleic acids, glycoproteins, carbohydrates, etc.

In one embodiment, this invention provides a method of sorting a fluid mixture comprising a plurality of polymers varying in terms of the physico-chemical characteristics of each of said plurality of biopolymers, said method comprising the steps of:
  a) loading a fluid mixture comprising a plurality of polymers in a molecular sorter comprising:
    i. a substrate;
    ii. a plurality of obstacles arranged at regular intervals in a plurality of rows, columns or combinations thereof on a surface of said substrate, wherein said obstacles are so arranged as to form gaps between said obstacles, with horizontal gaps being of a width less than vertical gaps between said obstacles, and said gaps form channels for fluid conductance, when fluid is introduced in said sorter;

iii. a sample inlet to said sorter;

iv. microfluidic channels in fluid communication with said channels;

viii. sample collection ports in fluid communication with said channels;

ix. at least a first conduit for applying an electrostatic force field or hydrodynamic force field parallel in direction to said rows;

x. at least a second conduit for applying an electrostatic force field or hydrodynamic force field parallel in direction to said columns, and perpendicular in direction to said rows; and b) applying said electrostatic force field or hydrodynamic force field parallel in direction to said rows, and said electrostatic force field or hydrodynamic force field parallel in direction to said columns, and perpendicular in direction to said rows, whereby applying said force fields allows for size-based separation of said plurality of biopolymers through said channels; and c) collecting separated biopolymers obtained in (b) from said sample collection ports.

In one embodiment, the invention provides an apparatus for quickly continuously fractionating biomolecules, such as DNAs, proteins and carbohydrates by taking advantage of differential bidirectional transport of biomolecules of different sizes through periodic arrays of microfabricated nanofilters.

The molecules for separation may be any which may be distinguished by the methods and via the devices of this invention. In one embodiment, a solution or buffered medium comprising the molecules may be used in the methods and for the devices of this invention. In one embodiment, such solutions or buffered media may comprise natural or synthetic compounds. In another embodiment, the solutions or buffered media may comprise supernatants or culture media, which in one embodiment, are harvested from cells, such as bacterial cultures, or in another embodiment, cultures of engineered cells, wherein in one embodiment, the cells express mutated proteins, or overexpress proteins, or other molecules of interest which may be thus applied. In another embodiment, the solutions or buffered media may comprise lysates or homogenates of cells or tissue, which in one embodiment, may be otherwise manipulated for example, wherein the lysates are subject to filtration, lipase or collagenase, etc., digestion, as will be understood by one skilled in the art, wherein a solution of desired molecules may be obtained and subjected to the methods of this invention.

It is to be understood that any complex mixture, comprising two or more molecules which differ in terms of their molecular size, charge, hydrophobicity, hydrophilicity, or any physical or chemical characteristic, or combinations thereof, whose separation is desired, may be used for the methods and in the sorters/devices of this invention, and represents an embodiment thereof.

In another embodiment, the solutions or buffered media for use according to the methods and for use in the devices of this invention may comprise any fluid, having molecules for separation with the described properties, for example, bodily fluids such as, in some embodiments, blood, urine, serum, lymph, saliva, anal and vaginal secretions, perspiration and semen, or in another embodiment, homogenates of solid tissues, as described, such as, for example, liver, spleen, bone marrow, lung, muscle, nervous system tissue, etc., and may be obtained from virtually any organism, including, for example mammals, rodents, bacteria, etc. In some embodiments, the solutions or buffered media may comprise environmental samples such as, for example, materials obtained from air, agricultural, water or soil sources, which are present in a fluid which can be subjected to the methods of this invention. In another embodiment, such samples may be biological warfare agent samples; research samples and may comprise, for example, glycoproteins, biotoxins, purified proteins, etc.

As will be appreciated by those in the art, virtually any experimental manipulation may have been done on the sample prior to its use in embodiments of the present invention. For example, a variety of manipulations may be performed to generate a liquid sample of sufficient quantity from a raw sample. In some embodiments, gas samples and aerosol samples are so processed to generate a liquid sample containing molecules whose separation may be accomplished according to the methods of this invention.

In one embodiment, the device is adapted such that analysis of a species of interest may be conducted, in one embodiment, in the sorter, or in another embodiment, downstream of the sorter. In one embodiment, analysis downstream of the sorter refers to removal of the sorted species from the device, and placement in an appropriate setting for analysis, or in another embodiment, construction of a conduit from the sorter, for example, from a collection port, which relays the sorted material to an appropriate setting for analysis. In one embodiment, such analysis may comprise signal acquisition, and in another embodiment, a data processor. In one embodiment, the signal can be a photon, electrical current/impedance measurement or change in measurements. It is to be understood that the sorting device of this invention may be useful in various analytical systems, including bioanalysis microsystems, due to its simplicity, performance, robustness, and integrabilty to other separation and detection systems, and any integration of the device into such a system is to be considered as part of this invention.

Figure 4:
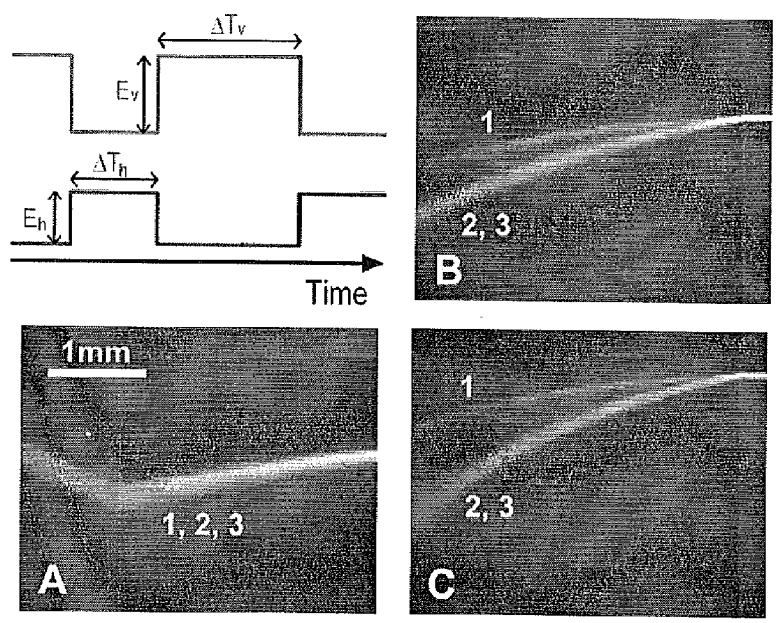
FIG. 4 shows fluorescence images of pulse field separation of SDS complexes inside an embodiment of the nanofilter matrix.

For example, as demonstrated herein in FIG. 3 or 4, when a mixture of fluorescently-labeled low density human lipoprotein (MW: 179 kDa), lectin phytohemagglutinin-L (MW: 120 kDa) and cholera toxin subunit B (MW: 11.4 kDa) were imaged following continuous- or pulse-field separation, the SDS-protein complexes separated into three different streams which were collected in different channels and routed to different reservoirs.

In one embodiment, the sorters/devices of this invention may be imaged with a two-dimensional detector. Imaging of the sorters/devices or parts thereof, may be accomplished by presenting it to a suitable apparatus for the collection of emitted signals, such as, in some embodiments, optical elements for the collection of light from the microchannels.

In another embodiment, the device is coupled to a separation system, or in another embodiment, a detection system, or in another embodiment, an analysis system or in another embodiment, a combination thereof. In another embodiment, the device is coupled to an illumination source.

In one embodiment, the sorter may be disposable, and in another embodiment, may be individually packaged, and in another embodiment, have a sample loading capacity of 1-50,000 individual fluid samples. In one embodiment, the sorter can be encased in a suitable housing, such as plastic, to provide a convenient and commercially-ready cartridge or cassette. In one embodiment, the sorter will have suitable features on or in the housing for inserting, guiding, and aligning the device, such that, for example, a sample loading compartment is aligned with a reservoir in another device, which is to be coupled to the sorter. For example, the sorter may be equipped with insertion slots, tracks, or a combination thereof, or other adaptations for automation of the sorting process via a device of this invention.

The sorter may be so adapted, in one embodiment, for high throughput sorting and analysis of multiple samples, such as will be useful in proteomics applications, as will be appreciated by one skilled in the art.

In one embodiment of the present invention, the sorter is a part of a larger system, which includes an apparatus to excite molecules inside the channels and detect and collect the resulting signals. In one embodiment, a laser beam may be focused upon the device, using a focusing lens, in another embodiment. The generated light signal from the molecules inside the device may be collected by focusing/collection lens, and, in another embodiment, reflected off a dichroic minor/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the concentrator. Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the concentrated species onto a display. In one embodiment, the data processor can also analyze the digital image to provide characterization information, such as size statistics, histograms, karyotypes, mapping, diagnostics information and display the information in suitable form for data readout.

In one embodiment, the steps of sorting for example, polypeptides obtained from a given cell, producing digestion products, and analyzing digestion products to determine protein sequence, can be performed in parallel and/or iteratively for a given sample, providing a proteome map of the cell from which the polypeptides were obtained. Proteome maps from multiple different cells can be compared to identify differentially expressed polypeptides in these cells, and in other embodiments, the cells may be subjected to various treatments, conditions, or extracted from various sources, with the proteome map thus generated reflecting differential protein expression as a result of the status of the cell.

In one embodiment, subsequent to separation via the methods and utilizing the devices of this invention, further analysis of the sorted materials is possible. Such analysis may be via direct coupling of the machinery necessary for such analysis to the outlet of a microchamber, as herein described, or in another embodiment, samples are processed separately.

In one embodiment such subsequent analysis, in addition, or in parallel to those already described, may comprise electrophoresis, chromatography, mass spectroscopy, sequencing (for example, for the identification of particular proteins or peptides), NMR and others, as will be appreciated by one skilled in the art.

In some embodiments, features of the present invention include: 1) arrays of nanofilters serve as the sieving media; 2) Ogston sieving mechanism within the nanofilter and the resulting differential bidirectional transport of biomolecules; 3) various operation methods of the nanofilter array chip (electrostatic force field based or hydrodynamic force field based with pulse-field operation mode or continuous-field operation mode).

In one embodiment, the electrostatic force field or hydrodynamic force field is applied in pulse-field operation mode, or in another embodiment, in continuous-field operation mode, as described and exemplified herein. In one embodiment voltage, pressure, timing or a combination thereof are varied, when sorting a sample. In one embodiment, the sample may be repetitively sorted, varying specific conditions with each sort, to further distinguish sorted species, for example, to obtain greater resolution in terms of size-dependent sorting, as a function of the timing, voltage, pressure, or other means, as will be appreciated by one skilled in the art, in the context of the devices and methods of this invention.

In another embodiment, the method further comprises the step of sorting a sample, wherein the pH or ionic strength of the buffered solution is varied at the time of sorting, as described.

In another embodiment, the method further comprises the step of sorting a sample, wherein the following parameters are modified:

1) Cross-sectional shape (or vertical profile) of the thin/thick regions can be rectangular-shaped to trapezoidal-shaped. This is determined by the fabrication process of the nanofilter matrix.

2) Different regions of the minimal sorting unit could have different nanofilters and different arrangement of the nanofilter arrays. (for example, different thin/thick channel thickness combination along the vertical direction of the minimal sorting unit).

3) Surface potential (surface charge density) can be changed/modulated by applying external potential to the substrate, as a gate potential.

In one embodiment, the methods and/or devices of this invention provide separation capability of small biomolecules, such as SDS-protein complexes, small double stranded DNA molecules (100 bp-2 Kb), undenatured proteins and carbohydrates, for example in FIGS. 3 and 4 demonstrated continuous-flow separation of SDS-protein complexes in a 60 nm nanofilter array chip under the continuous field separation mode (FIG. 3) and pulse-field separation mode (FIG. 4), respectively. Since with the same fabrication techniques, the nanofilter thin region depth can be further reduced down to ~10 nm; the present invention provides a means for size-based continuous-flow separation of small biomolecules such as proteins and carbohydrates by using an embodiment of the nanofilter array chip described herein. The invention, in one embodiment, thus provides a microfabricated molecular sieving chip that can size-fractionate small biomolecules such as SDS-protein complexes and small dsDNA molecules without using gel sieving matrices.

In another embodiment, the invention encompasses continuous-flow operation of the nanofilter array chip ideal for preparatory sample fractionation with increased sample throughput. The separation efficiency of the miniature nanofilter array chip is comparable to current state of the art systems (i.e. capillary gel electrophoresis) and because of their regular sieving structures, the nanofilter array chip can be further optimized based on the understanding about the sieving process during the passage of the molecules through the nanofilter.

In another embodiment, the devices of this invention can be used in continuous-flow separation of native proteins based on either the protein's charge or size, depending on the ionic strength of the buffer employed with the device. If the thickness of the electrical double layer, the Debye-length $\lambda_D$, is modulated to be comparable to the height of the nanochannel (e.g. under low ionic strength), similar sized biomolecules bearing different net charges will have different apparent diffusion coefficients through a nanochannel. Such charge-selective phenomena can be exploited with the devices of this invention, in some embodiments, in combination with active transport of biomolecules through the nanofluidic filter array, when operated at low ionic strength (1.3 mM).

For example, $SiO_2$-surfaces in some embodiments of the devices of this invention, are negatively charged, leading to surface charge dominated transport through nanochannels, where in this embodiment, biomolecules with a lower negative net charge can jump through nanofilters with a greater probability than biomolecules bearing a higher negative net charge, resulting in distinct streams through the devices in this embodiment. If the device according to this embodiment, is operated at high ionic strength (130 mM) where the Debye-length $\lambda_D$ is negligible, size-based separation of native proteins is expected, because steric interactions between the biomolecules and the nanofilter walls are dominant. In some embodiments, probe biomolecules that are smaller than the nanofilters, are separated due to Ogston sieving.

In another embodiment, the device is filled with low ionic strength buffer so that the thickness of the electrical double layer $\lambda_D$ is no longer negligible, as compared to the height of the shallow nanochannels $h_s$. At these ionic strengths co-ions are excluded and counterions are enriched in nanometer-sized apertures, called the exclusion-enrichment effect. This charge-selectivity favors proteins with lower negative net charge for passage compared to biomolecules with higher negative net charge, resulting in a bigger drift in the x-direction with decreasing net negative charge as exemplified herein.

In another embodiment, the nanofilter array chip may be batch-fabricated in a cleanroom environment, is chemically and mechanically robust, and can be used over a long period without degradation of its characteristics. The chemical nature of nanofilter array surface can be tailored for a specific biomolecule to be analyzed. The nanofilter array chip allows the use of different buffer systems, enabling the integration of different biomolecule sensors and separation and reaction chambers in one single chip, without the concern of sieving matrix crosstalk and contamination. The separation resolution of the nanofilter array chip can be further improved by scaling down the nanofilter. Since sub-100 nm resolution photolithography is now routinely performed in the microelectronics industry, such nanofilter array chip can be easily manufactured in a commercial setting.

The highlighted features listed above, inter-alia, make the nanofilter array chip an ideal candidate as a separation scheme for a truly integrated proteomic sample-preparation microsystem that includes fully integrated multiple separation and purification steps.

In another embodiment, the sorters/devices of this invention and methods of use thereof allow for size fractionation of smaller proteins out of a complex biomolecule sample. In serum analysis of biomarkers, it is essential to fractionate smaller signaling molecules out of larger structural proteins such as albumin. Dialysis membrane fraction is not ideal for this application since they tend to lose smaller, low-abundance proteins, and such methods are ideally suited for use with the sorters/devices and/or methods of this invention.

In another embodiment, the sorters/devices of this invention and methods of use thereof allow for size fractionation of carbohydrates. There is no well-established separation technique for carbohydrate and sugar molecules, which limits the development of potentially important biosensing and diagnostic tools based on sugar molecules. The sorters/devices of this invention can be engineered to provide good separation efficiency for sugar molecules, which is very difficult to separate and analyze with current conventional techniques.

In another embodiment, the sorters/devices of this invention and methods of use thereof allow for size fractionation of nanoparticles, nanotubes and other nanotechnology tools. Nanotechnology requires nanoparticles or nanotubes that are uniform in size and shape, while the chemical synthesis processes for these nanoparticles often generate particles that are diverse in size and shape. The sorters/devices of this invention are useful for separating different nanoparticles, based on their size and shape, to obtain pure, well-characterized groups of nanoparticles.

In another embodiment, the sorters/devices of this invention and methods of use thereof allow for DNA sequencing. The sequencing of DNA is performed by size-fractionation of a group of single stranded DNA using capillary gel electrophoresis with polymeric liquid sieving media. Since the separation efficiency and resolution of the sorters/devices of this invention is comparable to that of capillary gel electrophoresis, one could thus sequence the DNA without using liquid sieving media.

In another embodiment, the sorters/devices of this invention and methods of use thereof allow for rapid, continuous fractionation of any biomolecule, for example, nucleic acid, proteins, carbohydrates, etc., by taking advantage of differential bidirectional transport of biomolecules with varying physico-chemical characteristics, for example size, charge, hydrophobicity, or combinations thereof, through periodic arrays of microfabricated nanofilters. The passage of biomolecules through the nanofilter is a function, in some embodiments, of steric or electrostatic interactions between charged macromolecules and charged nanofilter walls. Continuous-flow separation through the sorters/devices of this invention are applicable for molecules varying in terms of any molecular properties (e.g., size, charge density or hydrophobicity) that can lead to differential transport across the nanofilters. Embodiments of this invention include methods of utilization thereof for the separation of such biomolecules.

In some embodiments, the separation methods/devices/sorters of this invention will include varying voltage or ionic strength of the solutions utilized, which in turn may optimize separation of the biomolecules to specific streams, and/or optimization of the resolution or discrete boundaries of each respective stream. This will be apparent to one skilled in the art, and embodiments of such optimization methods are exemplified hereinbelow.

The following examples are presented in order to more fully illustrate certain embodiments of the invention. They should in no way be construed, however, as limiting the broad scope of the invention.

EXAMPLES

Materials and Methods

Fluorescence Biomolecule Sample Preparation dsDNA samples were purchased from New England BioLabs (Beverly, Mass.). They were labeled with an intercalating fluorescence dye YOYO-1 (Molecular Probes) in TBE 5× buffer for fluorescence detection. The dye to DNA base pair ratio was about 1:20 and the final DNA concentration was about 12.76 µg/ml in the TBE 5× sample solution. Three different fluorescein or Alexa Fluor 488 conjugated proteins were purchased from Molecular Probes: cholera toxin subunit B, lectin phytohemagglutinin-L and low density human lipoprotein. The complete denaturation and dissociation of these proteins was performed by adding sodium dodecyl sulfate (SDS, Sigma) and dithiothreitol (DTT, Sigma) to the protein mixture. The SDS-DTT protein mixture contained 2 wt % SDS and 0.1M DDT and was treated in a 65° C. water bath for 10 minutes. The resultant SDS-protein complex solution was further diluted in TBE 5× buffer to a protein concentration of 40 μg/ml. This final SDS-protein complex sample solution contained 0.1 wt % SDS and 5 μM DTT.

Chip Design

The two-dimensional nanofilter based devices were designed in such a way that the initial main stream of biomolecules was injected though a thick channel from a top corner of the device. The fractionated components of the sample mixture were collected at intervals along the opposite edge. Many microfluidic channels were designed to surround the nanofilter arrays and connect them to fluid reservoirs, where voltages or pressures were applied. The channels provided sample loading and collection ports, and created horizontal and vertical force fields across the entire nanofilter matrix.

Chip Operation

Electrostatic force based or hydrodynamic-based force fields were applied to the devices in pulse-field or continuous-field mode. In the continuous-field operation mode, constant force field was applied across the nanofilter matrix during the separation process. The field distribution and strength was modulated by alternating the voltages/pressures applied at different fluidic reservoirs. In the pulse-field operation mode, the voltages/pressures of different strengths or durations were applied at different reservoirs to alternate the force field in the nanofilter matrix.

Example 1

Fabrication of an Embodiment of the Microseparator

To construct a device, which can continuously fractionate small biomolecules such as proteins based on their sizes, a nanofilter array chip was fabricated. The microchip comprising nanofilters, representing an embodiment of this invention, was constructed using conventional photolithography and reactive ion etching (RIE) techniques, with nanofilter gap thickness ($d_s$) as thin as 20 nm. The microchip was constructed to comprise thick channels (1-10) with width $L_d$ separated by rows of nanofilters (1-20) with width of $W_s$ and length $L_s$. Rectangle-shaped silicon pillars (1-30) were designed with width of $W_p$ to serve as supporting structures. The rows of nanofilters and silicon pillars may optionally have a lateral shift (FIG. 1A).

Figure 1:
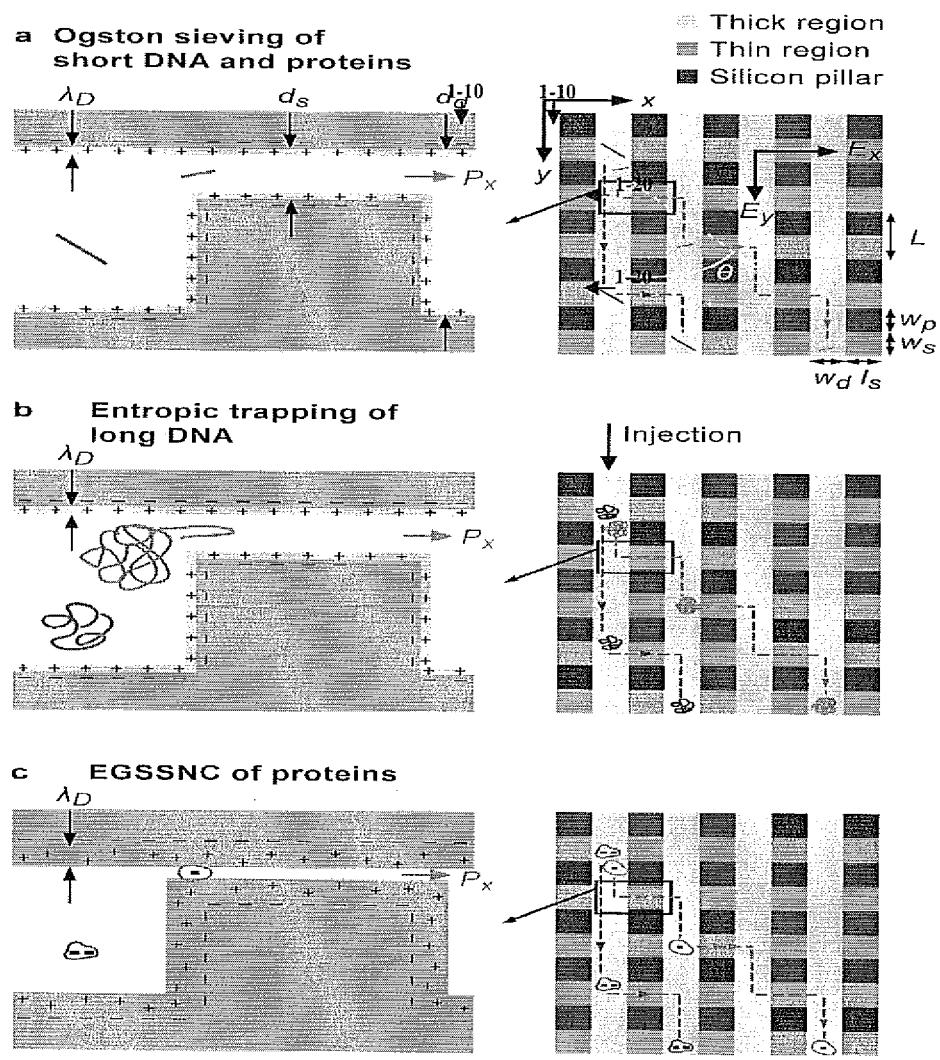
FIG. 1 schematically depicts negatively charged biomolecules assuming bidirectional motion in the ANA under the influence of two orthogonal electric fields Ex and Ey. On the left, cross-sections of the nanochannels are shown (lighter zones highlight the source of separation), whereas on the right different migration trajectories of biomolecules are presented in the top view of the ANA. Nanofilters (1-20) (with width ws, length ls, and depth ds) arranged in rows are separated by deep channels (1-10) (with width ld and depth dd). Rectangular pillars (1-30) (with width wp and length ls) between nanofilters serve as supporting structures to prevent collapse of the top ceiling. The Debye-length λD is the thickness of the electrical double layer, θ is the deflection angle, and L is the mean characteristic drift distance between two consecutive nanofilter crossings. a, Ogston sieving. Compared to larger DNA or larger native protein molecules, smaller ones are preferred for passage through the nanofilter due to their greater retained configurational freedom, resulting in a greater nanofilter jump passage rate Px. b, Entropic trapping. Longer DNA molecules have larger surface area contacting the nanofilter threshold, resulting in a greater probability for hernia formation and thus a greater nanofilter passage rate Px. c, Electrostatic governed separation by sample net charge for native proteins at low ionic strength. Electrostatic repulsion from the 55-nm-high channels is smaller for less negatively charged (green) than for more negatively charged native proteins (red), resulting in a greater passage rate Px for less negatively charged proteins.

The separation mechanism of the sorter relies on different sieving characteristics along two orthogonal directions within the sorter, which are set perpendicular and parallel to the nanofilter rows (indicated as x- and y-axis, respectively, in FIG. 1). Upon application of an electric field Ey along the positive y-axis, uniformly negative-charged molecules injected into the array assume a drift motion in deep channels with a negative velocity Vy that is size-independent. An orthogonal electric field Ex is superimposed along the negative x-axis across the nanofilters, and this field selectively drives the drifting molecules in the deep channel to jump across the nanofilter in the positive x-direction to the adjacent deep channel. Molecular crossings of the nanofilter under the influence of the electric field Ex can be described as biased thermally activated jumps across free energy barriers at the nanofilter threshold.

When molecules travel through the nanofilter, their passage is sterically hindered, due to the Ogston sieving process. For Ogston sieving, this energy barrier originates from the configurational entropy loss within the constriction due to the steric constraints of the nanofilter wall, and this barrier has been shown to favor molecules with a smaller size for passage (FIG. 1a), resulting in a greater jump passage rate Px for shorter molecules. Therefore shorter molecules exercise a shorter mean characteristic drift distance L in the deep channels between two consecutive nanofilter crossings, leading to a larger stream deflection angle θ.

A previous study on long DNA molecules trapped at a similar nanofluidic constriction showed that the activation free energy barrier for DNA escape depended solely on the inverse of the electric field strength (~1/Ex)27. Further, longer molecules have a larger surface area contacting the constriction and thus have a greater probability to form hernias that initiate the escape process (i.e., a higher escape attempt frequency) (FIG. 1b). Therefore, in the entropic trapping regime, longer molecules assume a greater jump passage rate Px, resulting in a larger deflection angle θ.

Figure 2A:
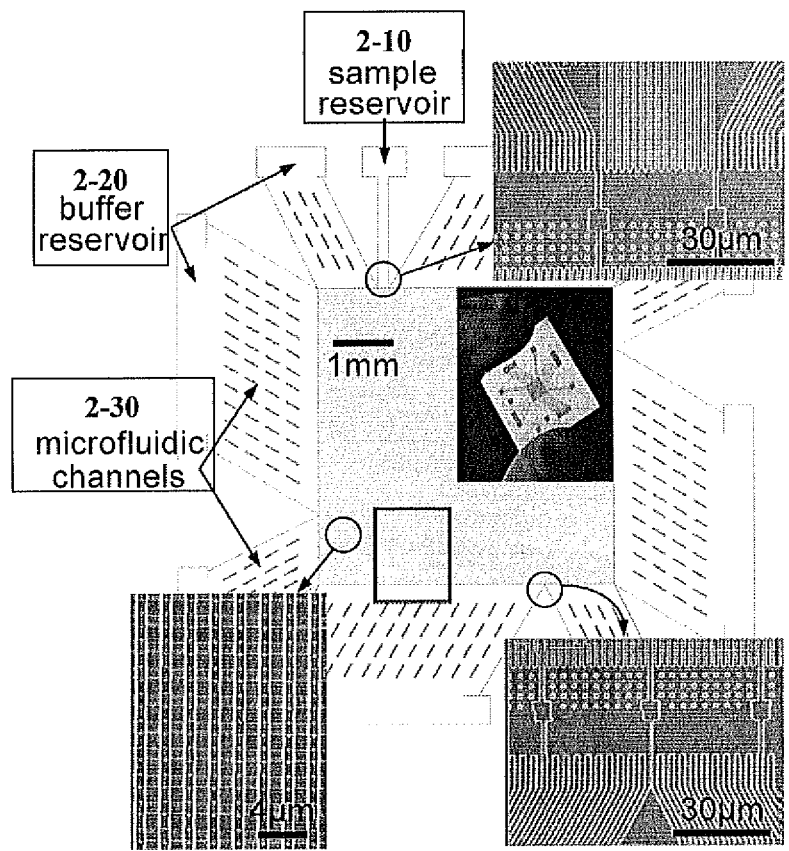
FIG. 2A depicts the structures of an embodiment of the microfabricated two-dimensional nanofilter based device illustrating the sieving matrix integrated with the microfluidic channels. Scanning electron microscopy images show details of different device regions (clockwise from top right: sample injection channels, sample collection channels, and minimal sorting unit). The separation chamber (consisted of rows of nanofilters) is 5 mm×5 mm, and the nanofilter has width (Ws) and length (Ls) both of fpm. The many microfluidic channels (2-30) connecting to buffer reservoirs (2-20) produce electrostatic force field or hydrodynamic force field over the sieving matrix by acting as electric-current injectors or fluidic flow injectors, which enables separation of materials introduced into the sample reservoir (2-10). The inset shows a photograph of the thumbnail-sized device. The rectangular ANA is 5 mm×5 mm, and nanofilters ($w_s$=1 µm, $l_s$=1 µm and $d_s$=55 nm) are spaced by 1 µm×1 µm square-shaped silicon pillars. Deep channels are 1 µm wide and 300 nm deep. Injection channels connecting sample reservoir inject biomolecule samples as a 30 µm wide stream. Injection channels are 1 mm from the top left corner. The red rectangle highlights the area in which the fluorescence photographs in FIG. 5 were taken.
Figure 2B:
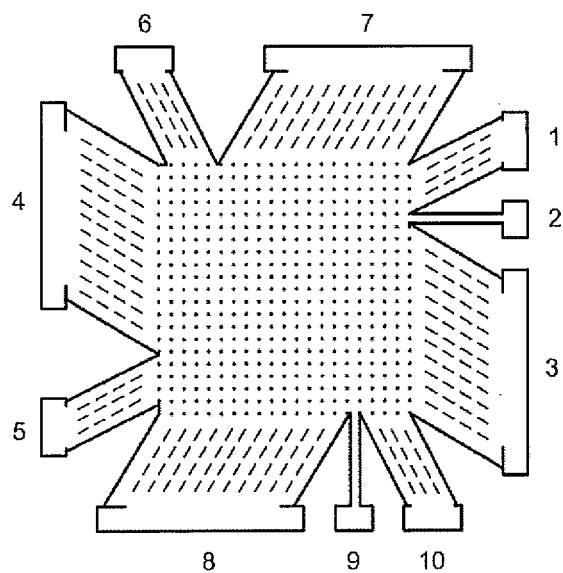
FIG. 2B depicts the operation of an embodiment of the chip involving application of horizontal and vertical force fields across the entire nanofilter matrix. The four sides of the separation chamber are connected to the fluid reservoirs with microfluidic channels (left: reservoir port 1, 2, 3; right: reservoir port 4, 5; top: reservoir port 6, 7; bottom: reservoir port 8, 9, 10). Different voltages or pressures can be applied at the fluid reservoirs to generate the two-dimensional force field pattern.

The two-dimensional nanofilter based devices have been designed in such a way that the initial main stream of biomolecules is injected though a thick channel (2-10) from a top corner of the device. The fractionated components of the sample mixture are collected at intervals along the opposite edge (FIG. 2). Many microfluidic channels (2-30) are designed to surround the nanofilter arrays and connect them to fluid reservoirs (2-20), where voltages or pressures are applied. The channels provide sample loading and collection ports, and they create horizontal and vertical force fields across the entire nanofilter matrix, which is necessary for the operation of the nanofilter arrays.

One embodiment of such a device is shown in FIG. 2, where the separation chamber (consisted of rows of nanofilters) was 5 mm×5 mm, and the nanofilter had a width (Ws) and length (Ls) both of 1 μm. The nanofilters were spaced by 1 μm×1 μm square-shaped silicon pillars. There was no lateral shift between nanofilter rows in the device. The many microfluidic channels connecting to buffer reservoirs produced an electrostatic force field or hydrodynamic force field over the sieving matrix by acting as electric-current injectors or fluidic flow injectors.

In one embodiment, the device contains nanofilters with a constriction size of 55 nm. Deep channels separating the nanofilter rows are 1 μm wide and 300 nm deep. The initial biomolecule stream is continuously injected into the deep channels on the top left of the device. The fractionated biomolecule streams are collected at intervals along the opposite edge. Microfluidic channels surrounding the sorter connect to fluid reservoirs, where voltages are applied. The microfluidic channels provide sample loading and collection ports, and further act as electric-current injectors to create uniform horizontal and vertical electric fields over the device structure.

For operation of the device, the force fields can be electrostatic force based or hydrodynamic force based, and both of them can be operated in pulse-field mode or continuous-field mode. In the continuous-field operation mode, constant force field is applied across the nanofilter matrix during the separation process. The field distribution and strength can be modulated by alternating the voltages/pressures applied at different fluidic reservoirs. In the pulse-field operation mode, the voltages/pressures of different strengths or durations will be applied at different reservoirs to alternate the force field in the nanofilter matrix.

According to this embodiment, illustrated in FIG. 2, operation of the chip involves application of horizontal and vertical force fields across the entire nanofilter matrix. The four sides of the separation chamber are connected to the fluid reservoirs with microfluidic channels (2-30) (left: reservoir port 1, 2, 3; right: reservoir port 4, 5; top: reservoir port 6, 7; bottom: reservoir port 8, 9, 10). Different voltages or pressures can be applied at the fluid reservoirs (2-20) to generate the two-dimensional force field pattern.

Example 2

Operation of the Microseparator in Continuous-Field Mode

Molecules that can be separated in such a chip include, but are not limited to, proteins and DNA, RNA, carbohydrate (sugar), nanoparticles, and small organelles.

Optimal sieving with a nanofilter is expected when the molecule size is comparable with the nanofilter thin gap size. However, the gap size of the nanofilter does not have to be smaller than the size of the molecule. Indeed, the separation of SDS-proteins (typically ~10 nm in physical dimensions) using nanofilters as large as 60 nm is feasible. If one wishes to separate different (larger or smaller) biomoelcules in this chip, nanofilter gap size can be adapted to the molecules to be separated.

To demonstrate continuous-flow separation of small biomolecules with the invention of the nanofilter array chip SDS-protein complexes and small double-stranded DNA molecules were separated using a microchip, as depicted in FIG. 2, in continuous field separation mode (FIG. 3). In the electrostatic force-based continuous field separation mode, constant field is applied across the nanofilter arrays during the separation process. The field distribution and strength can be modulated by alternating the voltages applied at different fluidic reservoirs.

Fluorescence images of continuous field separation of SDS-protein complexes inside the 2-D nanofilter based matrix shows three distinct bands, with the following assignment for the SDS-protein complexes: (1) low density human lipoprotein (MW: 179 kDa); (2) lectin phytohemagglutinin-L (MW: 120 kDa); (3) cholera toxin subunit B (MW: 11.41 kDa). When only a horizontal field was applied (Eh=300 V/cm), no observable separation between the three complexes occurs, however three distinct species are resolved when both horizontal and vertical fields were applied (Eh=200 V/cm, Ev=100 V/cm). Separated molecules were collected in different channels and routed to different reservoirs, as designed in this embodiment of the chip.

Example 3

Operation of the Microseparator in Pulse-Field Separation Mode

In another embodiment of the microseparator, separation can also be achieved using alternating electric fields of different strengths and/or durations in the pulse-field separation mode (FIG. 4). In the embodiment presented here, the voltage was applied at different reservoirs, where the horizontal electric field (Eh) alternated with the vertical electric field (Ev), and increasing the duration of the vertical force field enhanced the separation. Thus more size-differential jumpings over the nanofilters were experienced in the case of longer duration of the vertical electric field.

While many different artificial molecular sieving matrixes are known in the art for size-fractionation of biomolecules based on different mechanisms, to date, microfabricated artificial sieving systems have been limited for separation of large biomolecules such as viral DNA, mainly because it is generally challenging to fabricate sieves with comparable molecular dimensions.

Typical proteins have molecular dimensions of 1-5 nm, and while there are several reports on the fabrication of nanofluidic channels as small as 10 nm, it is generally challenging to fabricate such nanofluidic structures.

In the nanofilter array chip of this invention, however, the batch fabrication method of the nanofilters was incorporated with a novel sample loading and separation scheme, thus uniquely separates small biomolecules, such as SDS-protein complexes, small double stranded DNA molecules (100 bp-2 Kb), undenatured proteins and carbohydrates, in either continuous field separation mode or pulse-field separation mode.

Since with the same fabrication techniques, the nanofilter thin region depth can be further reduced down to ~10 nm, it is possible to achieve size-based continuous-flow separation of small biomolecules such as proteins and carbohydrates by using the nanofilter array chip. This is therefore the first microfabricated molecular sieving chip that can size-fractionate small biomolecules such as SDS-protein complexes and small dsDNA molecules without using gel sieving matrices.

The continuous-flow operation of the nanofilter array chip is ideal for preparatory sample fractionation with increased sample throughput. The separation efficiency of the miniature nanofilter array chip is comparable to current state of the art systems (i.e. capillary gel electrophoresis). Because of their regular sieving structures, the nanofilter array chip can be further optimized based on the understanding about the sieving process during the passage of the molecules through the nanofilter.

Another advantage to the array chip presented here is the ability to batch-fabricate it in a cleanroom environment, that it is chemically and mechanically robust, and can be used over a long period without degradation of its characteristics. The chemical nature of nanofilter array surface can also be tailored for a specific biomolecule to be analyzed.

The microseparators described herein allow for the use of different buffer systems, therefore enabling integration of different sensors and separation and reaction chambers in a single chip, without sieving matrix crosstalk and contamination. Moreover, the microseparators described herein may serve as part of a "lab on a chip" scenario, with a truly integrated proteomic sample-preparation microsystem that includes fully integrated multiple separation and purification steps.

Example 4

Operation of the Microseparator in Continuous-Field Mode

Figure 5:
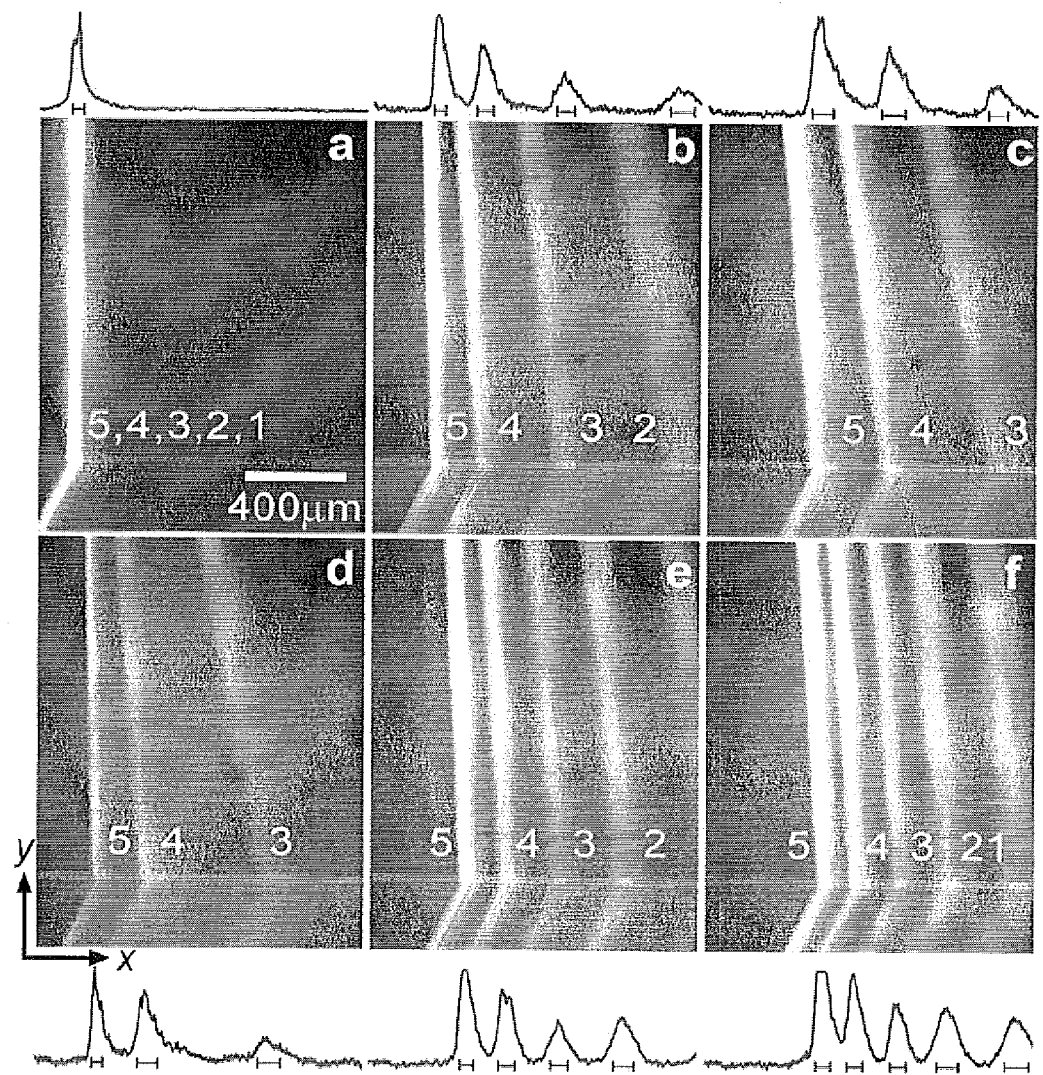
FIG. 5 demonstrates Ogston sieving of PCR markers through the device. Fluorescent photographs of the PCR marker stream pattern were taken in the area highlighted by the red rectangle in FIG. 2. For a, $E_x$: floated, $E_y$=25 V/cm; for b, $E_x$=35 V/cm, $E_y$=25 V/cm; for c, $E_x$=60 V/cm, 4=25 V/cm.

In another embodiment of the device and its operation, a PCR marker sample was introduced into the device under a broad range of field conditions (FIG. 5). PCR markers which contained 5 different DNA fragments of sizes ranging from 50- to 766-base pairs (bp) were used. Since the persistence length of DNA is about 50 nm (about the contour length of 150-bp DNA), the PCR marker fragments appear relatively straight, and recognizable as rigid, rod-like molecules with an end-to-end distance of about 16 nm to 150 nm. The entry into the confining nanofilter can be realized if the rod-like DNA molecules are properly positioned and oriented without overlapping the wall, which limits the configurational freedom and creates an entropic barrier (i.e., Ogston sieving). FIG. 5a-5f are fluorescence photographs of the PCR marker stream pattern in the device when horizontal and vertical fields of different values were applied. The horizontal field $E_x$ quickly deflected DNA fragments according to their sizes, with the stream deflection angle θ and the stream width W depending on the exact field conditions. Increasing the horizontal field $E_x$ resulted in larger deflection angles as well as wider spreading of the streams. Increasing $E_x$ enhanced the jump passage rate $P_x$, leading to a shorter drift distance L and thus a larger deflection angle θ.

The vertical electric field $E_y$ also affects the deflection angle θ. As $E_y$ was raised from 25 V/cm to 75 V/cm at fixed $E_x$=35 V/cm (FIG. 5d-5f), the DNA stream pattern became more focused with shorter DNA fragments (50-bp, 150-bp) shifting towards the negative x direction and longer DNA fragments (300-bp, 500-bp, 766-bp) shifting towards the positive. A greater vertical field $E_y$ shortens the time for DNA to explore the transition through a nanofilter threshold, which explains the behavior of short DNA with increased $E_y$. The long DNA fragments shifted reproducibly with ($E_y$ up to 125 V/cm), which in one embodiment, is due to the slight field non-uniformity in the device.

Example 5

Entropic Trapping of Large Molecules

In another embodiment of the device and its operation, large molecules, for example, long DNA molecules, can be separated based on an entropic trapping mechanism. Toward this end, a λ DNA-Hind III digest was prepared, which contained 6 DNA fragments with sizes ranging from 2.027- to 23.13-kilobase pairs (kbp) and corresponding radii of gyration $R_g$ of about 140 nm to 520 nm.

These radii are greater than the nanofilter constriction size in the device according to this embodiment, and therefore the nanofilter jump dynamics necessarily involved deformation and hernia nucleation (i.e., entropic trapping) of the molecules. With application of a horizontal field of $E_x$=185 V/cm and a vertical field of $E_y$=100 V/cm, the λ DNA-Hind III digest was separated in less than 1 minute with base-line resolution (FIG. 6a-6b, note the shortest 2.027-kbp fragment was too dim for clear visualization in the figure, but using a higher CCD gain setting and longer CCD exposure time, the 2.027-kbp fragment was identified to be base-line separated with the others).

Time-lapse video studies revealed that, as expected, longer DNA fragments followed more deflected migration trajectories than shorter ones, a clear distinction of entropic trapping from Ogston sieving. A threshold value for the horizontal field was observed, $E_{x,c}$ (~15 V/cm), below which long DNA molecules were virtually completely confined in the deep channels (FIG. 6g). This threshold phenomenon, in some embodiments, is due to the difficulty of hernia formation in a low field regime, since the constriction size of 55 nm is comparable to the DNA persistence length. The streams of λ DNA-Hind III digest followed more deflected and resolved trajectories as $E_x$ was increased (FIG. 6c-6f), an observation, which is, in some embodiments, consistent with the argument that increased $E_x$ lowers the activation energy barrier leading to a higher jump passage rate $P_x$.

Example 6

Separation of Protein Complexes

In some embodiments, the device is capable of separating mixtures of proteins that have different molecular weights (MW). Two Alexa Fluor 488-conjugated protein complexes were prepared: cholera toxin subunit B (MW~11.4-kDa) and β-galactosidase (MW~116.3-kDa). The complexes were denatured with sodium dodecyl sulfate (SDS) and dithiothreitol (DTT), and applied to the device, as in the previous example. A horizontal field of $E_x$=75 V/cm and vertical field of $E_y$=50 V/cm were applied, and the SDS-protein complexes were base-line separated into 2 streams within 2 minutes. The protein stream widths at 1 mm, 3 mm, and 5 mm from the injection point corresponded to resolutions $R_s$ of 0.57, 0.94 and 1.47, respectively (FIG. 7a). Cholera toxin subunit B was deflected more than β-galactosidase in all the experiments, suggesting Ogston sieving to account for the jump dynamics of these linear protein complexes (FIG. 7b). Further increasing $E_x$ resulted in larger lateral separation between the two streams. However, resolution $R_s$ was compromised due to broader lateral diffusion, as evidenced by the decrease in the resolution curve (FIG. 7b). The separation resolution for proteins may also be improved by increasing separation distance.

Example 7

Relationships between Ogsten Sieving and Entropic Trapping

In some embodiments, a transition between Ogston sieving and entropic trapping may occur with the devices of this invention. The trajectories of different-sized DNA molecules, for example, are consistent with either Ogston sieving or entropic trapping (FIG. 8a). Crossover from Ogston sieving to entropic trapping in the device may occur as molecular size or confinement increases, and the transition regime, for example, with the present studies involving DNA can be estimated to be between 1-kbp to 2-kbp, which is concurrent with the transition of DNA rod-like conformations to coiled conformations.

In the Ogston sieving regime, the nanofilter jump passage rate $P_x$ for short DNA of a by number N can be calculated based on the equilibrium partitioning theory and the Kramers rate theory. In the limit of low field, the passage rate $P_x$ is proportional to $E_x^2$ K/N, where K is the DNA equilibrium partitioning coefficient that is calculated as the ratio of accessible microscopic configuration state integrals within shallow and deep regions across the nanofilter.

The relative mobility $\mu_x^*$ along the x-axis across the nanofilters can be calculated as:

$$\mu_x^* = \left(1 + \frac{\alpha N}{E_x K}\right)^{-1} \quad \text{(Eq. 7-1)}$$

where α is a constant with a unit of V/(m·bp). By definition, $\mu_x^*$ is the ratio between the mobility $\mu_x$ along the x-axis and the maximum sieving free mobility $\mu_{x,max}$ across a nanofilter. Thus, the tangent of the stream deflection angle θ can be approximately written as:

$$\tan\theta = \frac{V_x}{V_y} = \frac{\mu_{x,max}}{\mu_0} \cdot \frac{E_x}{E_y} \cdot \mu_x^* = \frac{\mu_{x,max}}{\mu_0} \cdot \frac{E_x}{E_y} \cdot \left(1 + \frac{\alpha N}{E_x K}\right)^{-1} \quad \text{(Eq. 7-2)}$$

where $V_x$ and $V_y$ are the migration velocities along the positive x- and negative y-axis, respectively, and $\mu_0$ is the free solution mobility. In Eq. (7-2), DNA fragments were assumed to preserve their free draining property in the device deep regions along the y-axis. $\mu_{x,max}/\mu_0$ depends on the structural parameters of the ANA, and $\mu_{x,max}/\mu_0 = 4d_s d_d/(d_s+d_d)^2 = 0.52$ for the device tested in the described examples.

The equilibrium partitioning coefficient K can be calculated as in Fu et al. (Fu, J., Yoo, J. & Han, J. Phys. Rev. Lett. 97, art. no. 018103 (2006)). When small molecules, such as short DNA are used, Eq. (7-2) becomes tan $\theta=0.52E_x/E_y$, which indicates a sieving free case in the device.

The values obtained for tan $\theta$ for the PCR maker sample in FIG. 9 agreed with the curves calculated from Eq. (7-2). The best fitting constant $\alpha$ was found to be fairly constant for the different DNA fragments. The slight deviation of the theoretical curves from the deflection angle data in the low $E_x$ regime might be attributed to the field non-uniformity in the device.

Based on the calculation of $P_x$, a course-grained kinetic model was constructed that, in some embodiments, explain the field-dependent stream deflection angle $\theta$ of the PCR marker fragments (FIG. 9).

From the fluorescence intensity profile of FIG. 5b, the coefficients of variation (CVs) for the 150-bp, 300-bp, and 500-bp DNA stream profiles are 8.6, 6.0, and 4.5%, respectively. Therefore the size selectivity of the ANA in the Ogston sieving regime is about 5 nm (corresponding to the end-to-end distance of 20-bp DNA). The separation efficiency of the device can be further characterized by the effective peak capacity $n_c$ that defines the maximum number of separated streams that fit into the space provided by the separation. FIG. 8b shows the dependence of $n_c$ on the horizontal field $E_x$ where $n_c$ initially increased quickly with $E_x$ and then leveled off with an upper bound value of about 17. This asymptotic behavior of $n_c$ can be largely attributed to the DNA stream widening with increased $E_x$, which cancels out the increased lateral separation between the streams.

The effective peak capacity $n_c$ for $\lambda$ DNA-Hind III digest as a function of $E_x$ was plotted (FIG. 8b) The $n_c$ curve appears similar to the one observed for Ogston sieving, with an upper bound value of about 15.

Continuous-flow separation through the devices of this invention should be applicable to other molecular properties (e.g., charge density or hydrophobicity) that can lead to differential transport across the nanofilters. The continuous-flow operation of the device permits continuous-harvesting of the subset of biomolecules of interest to enhance the specificity and sensitivity of downstream biosensing and detection. The high-resolution separation and ease of sample collection may prove useful for preparative separation of complex biological samples, which has promising implications for, inter alia, proteomic research and biomarker discovery. The sample throughput of the device can be further scaled up by parallelism with multi-device processing. Devices of this invention, in some embodiments, can be used as a generic sieving structure to separate other particles of interest with nanoscale dimensions, including nanoparticles and nanowires, viruses and cell organelles.

Example 7

Separations with Varying Ionic Strength Buffers

Two different concentrations of Tris-Borate-EDTA buffer (TBE, Sigma-Aldrich) were chosen: high ionic strength measurements were performed at TBE 5× (equivalent ionic strength=130 mM,[22] $\lambda_D \approx 0.84$ nm), and TBE 0.05× was used as low ionic strength buffer (equivalent ionic strength=1.3 mM,[22] $\lambda_D \approx 8.4$ nm). The pH of the buffer was adjusted to 9.6 by addition of potassium hydroxide and the chips were electroosmotically flushed with the corresponding solution for more than 24 hours before use. The following commercially available proteins were investigated: B-phycoerythrin (Alexis Biochemicals) which is fluorescent with molecular weight (MW) 240 kDa (value from manufacturer) and pI=4.2-4.4; fibrinogen labeled with Alexa Fluor 488 (Molecular Probes) with MW 340 kDa and pI=5.5; lectin from *Lens culinaris* (lentil) FITC conjugate (Sigma-Aldrich) with MW 49 kDa and pI=8.0 for the acidic band lectin, pI=8.5 for the middle band lectin, and pI=8.8 for the basic band lectin; streptavidin labeled with Alexa Fluor 488 (Molecular Probes) with MW 52.8 kDa and pI=5-6. The protein concentration was 0.1-0.2 mg/ml and only the lectin was used at a higher concentration of 0.2-0.4 mg/ml due to its lower fluorescence intensity compared to the other proteins. These concentrations were chosen for a good signal-to-background ratio, and working at lower concentration does not affect their separation behavior. Fluorescence measurements were performed using an inverted epifluorescence microscope (IX-71, Olympus) with a 20× objective (numerical aperture 0.45) or a 10× objective (numerical aperture 0.3) illuminated by a 100 W mercury lamp (Chiu Technical Corp.). B-phycoerythrin was visualized with a Texas Red® filter set (excitation 562 nm, emission 624 nm, Semrock) whereas all other proteins were observed using a FITC filter set (excitation 482 nm, emission 536 nm, Semrock). Images were taken with a digital CCD camera (ORCA-ER, Hamamatsu Photonics) and analyzed with IPLab (Scanalytics). Background fluorescence levels were subtracted, and a moving average was applied for the fluorescence intensity cross-sections.

Size-based separation of fibrinogen (MW 340 kDa), B-phycoerythrin (MW 240 kDa), and lectin (MW 49 kDa) was obtained using the higher ionic strength buffer (TBE 5×) as presented in FIG. 10. The sample was injected at the top left of the image in FIG. 10(a) with the vertical electric field $E_y$ using electroosmotic flow and separated by the horizontal field $E_x$. The cross-section through the array along the dashed lines at the bottom of the images in FIG. 10(a) is shown in FIG. 10(b), where the black line represents FITC and the grey line Texas Red® fluorescence intensities. Three streams of the native proteins can be distinguished, corresponding to the molecular size of the biomolecules. The largest protein, fibrinogen, is least deflected in the x-direction whereas the smallest investigated biomolecule, lectin, was deflected the most. This increase in deflection is caused by 55-nm-high channels acting as entropic barriers, and the possibility to overcome these nanochannels increases with decreasing molecular size, consistent with an Ogston sieving mechanism.

The separation distance between the protein streams is dependent on the applied electric fields $E_x$ and $E_y$ which is shown in FIG. 11(a) for fibrinogen and B-phycoerythrin. For a fixed $E_y$, the curve indicates a maximal separation distance for a specific $E_x$, and this maximum increases with decreasing $E_y$. To discuss this behavior the Peclet number Pe is considered which represents the ratio of convective to diffusional transport:

$$Pe = \frac{lv}{D},$$

where l is the characteristic length, D the diffusion coefficient of the biomolecule, and v the electroosmotic velocity which decreases from 47.6 μm/s to 7.2 μm/s when decreasing $E_y$ from 100 V/cm to 16.5 V/cm. The Peclet number describes that efficient mixing is obtained for Pe ? 1, and distinct separations result for Pe=1, because diffusion is dominant, which results in increased interactions of the proteins with the nanofilters. Small separation distances are observed in FIG. 11(a) for low $E_x/E_y$ ratios because the small deflection in x-direction does not result in a large enough number of sieving events with the 55-nm-high channels. High ratios of horizontal to vertical electric field result in high values of the Peclet number, which makes good separations impossible. An optimal $E_x/E_y$ ratio can be found at which the number of sieving events is high and Pe low, resulting in maximal separations distances. For small values of $E_y$, increased separation distances are observed, because the Peclet number is small, electroosmotic flow reduced, and diffusional transport dominant. The counterpart of the increased diffusion is the broadening of the stream as shown in FIG. 11(b) for B-phycoerythrin, where the standard deviation σ is half the width of the stream. The standard deviation σ not only increases with decreasing $E_y$, but also with increasing $E_x$ because of the larger number of nanofilters through which the proteins have to pass.

Charge-based separation of native protein molecules has been achieved at TBE 0.05×. To exclude size-based separation effects, two biomolecules with approximately the same MW and different pI values were investigated: streptavidin with MW 52.8 kDa and pI=5-6, and lectin with MW 49 kDa and pI=8.0-8.8. The left image of FIG. 12(a) presents that at TBE 0.05× a charge-based separation of streptavidin and lectin has been obtained due to the difference in pI values. The pH value of the TBE buffer was 9.6 which is higher than the pI values of both proteins, resulting in negative net charges for both biomolecules. Streptavidin has a lower pI value than lectin and is therefore more negatively charged. This increased negative net charge results in a larger repulsion from the nanofilter walls, and in a lower deflection in x-direction. As a reference, no separation has been observed at TBE 5× between streptavidin and lectin [right image of FIG. 12(a)], which shows that differences in the MW of 3.8 kDa can not be resolved via this embodiment of the device.

Taken together, these results indicated that the size difference between the two proteins does not affect their separation obtained at low ionic strength, and is thus a charge-based separation process. The increased bending of the streams at low compared to high ionic strength in FIG. 12(a) indicates the electric field distribution was more inhomogeneous at TBE 0.05×. FIG. 12(b) presents the fluorescence intensity along the dotted lines in the images of FIG. 12(a) for TBE 0.05× (black line) and TBE 5× (grey line).

At low ionic strength charge-based separation was demonstrated for B-phycoerythrin, fibrinogen, and lectin (FIG. 13a). The left image shows separation of fibrinogen and lectin, which are fluorescent in the green range, and the right image corresponds to the orange-fluorescent B-phycoerythrin. The buffer was TBE 0.05×, pH=9.6, accordingly these proteins were negatively charged. B-phycoerythrin with pI=4.2-4.4 bears the highest net charge out of the investigated proteins and was therefore most repelled from the charge-selective 55-nm-high channels, leading to a small deflection in x-direction. The pI value of fibrinogen was 5.5 due to which its deflection along the x-axis was increased as compared to B-phycoerythrin. Lectin has pI values 8.0, 8.5, and 8.8 (acidic, middle, and basic band lectin) and therefore bears the lowest negative net charges out of the used biomolecules, resulting in the lowest repulsion from the nanofilter walls and their largest deflection in x-direction which is shown in FIG. 13(b). In this graph the fluorescence intensity of the dashed lines in FIG. 13(a) is plotted for the FITC filter set (black) and Texas Red® filter set (grey). The peak of lectin is not as sharp as the peaks of the other proteins because lectin from *Lens culinais* (lentil) contains acidic, middle, and basic band lectin which have not been fully separated but only widened on this ANA (not at TBE 5×, refer to FIG. 11). Compared to the results at high ionic strength (FIG. 11), the streams of fibrinogen and B-phycoerythrin are reversed because at low ionic strength it is no longer the molecular size but the pI value of the protein which determines the separation. It has to be annotated that the electric field strengths at low and high ionic strength can not be compared because the electroosmotic flow increases with dilution. These increased flow rates at TBE 0.05× lead to a typical residence time of 13 s (velocity=384.6 μm/s) of the proteins in the whole ANA.

Charge-based separation resolution $R_s$ can be improved by increasing the number of nanofilters through which the sieving is taking place. This improvement is obtained by increasing the field $E_x$ while keeping $E_y$ constant as shown in FIG. 14. The separation resolution between two streams (a and b) is defined as $$R_s = \frac{\Delta x}{2(\sigma_a + \sigma_b)},$$

where Δx is the spatial distance between the two streams.

Taken together, these results indicate that the separation at TBE 0.05× is charge-based.

In some embodiments, separation may be improved by optimizing the following parameters: increasing the electric field may improve the charge-based resolution; decreasing the height of the channels; and/or by using a gate electrode to actively control the surface potential.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A biomolecular sorter comprising:
   a) a substrate;
   b) a plurality of obstacles arranged at regular intervals in a plurality of rows, columns or combinations thereof on a surface of said substrate;
   c) a sample inlet to said sorter;
   d) at least a first conduit for applying an electrostatic force field or hydrodynamic force field parallel in direction to said rows; and
   e) at least a second conduit for applying an electrostatic force field or hydrodynamic force field parallel in direction to said columns, and perpendicular in direction to said rows;
   wherein said obstacles are so arranged as to form gaps between said obstacles, with horizontal gaps being of a depth less than vertical gaps between said obstacles, the depth of the horizontal gaps is at most 10 nm, said at least a first conduit and said at least a second conduit provide said electrostatic force field or hydrodynamic force field to a sieving matrix by acting as electro-current injectors or fluidic flow injectors which enables separation of materials introduced by a sample provided, wherein a fabrication process of said matrix defines a specified geometrical shape of a cross-section of said rows, said gaps comprise a first set of regions that includes nanofilters and a second set of regions that includes microfluidic channels, said sample transits through said first set and second set of regions, said first set of regions provides steric hindrance of said sample through said transit.

2. The sorter of claim 1, wherein said depth of said vertical gaps are from about 0.1-10 µm.

3. The sorter of claim 1, wherein said obstacles in said rows are laterally shifted with respect to each row.

4. The sorter of claim 1, wherein said gaps form channels for fluid conductance, when fluid is introduced in said sorter.

5. The sorter of claim 4, comprising microfluidic channels in fluid communication with said channels.

6. The sorter of claim 5, wherein said channels comprise sample loading ports.

7. The sorter of claim 5, wherein said channels comprise sample collection ports.

8. The sorter of claim 5, wherein said microfluidic channels are in fluid communication with a reservoir.

9. The sorter of claim 8, wherein voltage is applied to said reservoir.

10. The sorter of claim 9, wherein said applied voltage is less than 1000 V.

11. The sorter of claim 8, wherein pressure is applied to said reservoir.

12. The sorter of claim 1, wherein said electrostatic force field or hydrodynamic force field is applied in pulse-field operation mode.

13. The sorter of claim 1, wherein said electrostatic force field or hydrodynamic force field is applied in continuous-field operation mode.

14. The sorter of claim 1, wherein said substrate comprises silicon.

15. A microchip comprising the sorter of claim 1.

16. A method of sorting a fluid mixture comprising a plurality of biopolymers, which vary in terms of the physico-chemical characteristics of each of said plurality of biopolymers, said method comprising the steps of:
   f) loading a fluid mixture comprising a plurality of biopolymers in a biomolecular sorter comprising:
      i. a substrate;
      ii. a plurality of obstacles arranged at regular intervals in a plurality of rows, columns or combinations thereof on a surface of said substrate, wherein said obstacles are so arranged as to form gaps between said obstacles, with horizontal gaps being of a depth less than vertical gaps between said obstacles, and said gaps form channels for fluid conductance, when fluid is introduced in said sorter, the depth of the horizontal gaps is at most 10 nm;
      iii. a sample inlet to said sorter;
      iv. microfluidic channels in fluid communication with said channels;
      v. sample collection ports in fluid communication with said channels;
      vi. at least a first conduit for applying an electrostatic force field or hydrodynamic force field parallel in direction to said rows;
      vii. at least a second conduit for applying an electrostatic force field or hydrodynamic force field parallel in direction to said columns, and perpendicular in direction to said rows; and
   g) applying said electrostatic force field or hydrodynamic force field parallel in direction to said rows, and said electrostatic force field or hydrodynamic force field parallel in direction to said columns, and perpendicular in direction to said rows, whereby applying said force fields allows for separation of said plurality of biopolymers through said channels, said at least a first conduit and said at least a second conduit provide said electrostatic force field or hydrodynamic force field to a sieving matrix by acting as electro-current injectors or fluidic flow injectors which enables separation of materials introduced by said biopolymers, wherein a fabrication process of said matrix defines a specified geometrical shape of a cross-section of said rows, said gaps comprise a first set of regions that includes nanofilters and a second set of regions that includes microfluidic channels, said biopolymers transit through said first set and second set of regions, said first set of regions provides steric hindrance of said biopolymers through said transit; and
   h) collecting separated biopolymers obtained in (b) from said sample collection ports.

17. The method of claim 16, wherein said electrostatic force field parallel in direction to said rows provides an electroosmotic driving force for said fluid.

18. The method of claim 16, wherein said fluid has an ionic strength of about 1-1000 mM.

19. The method of claim 18, wherein said sorting is size-based.

20. The method of claim 16, wherein said physico-chemical characteristics comprise size, charge, hydrophobicity, hydrophilicity, or a combination thereof.

21. The method of claim 16, wherein said sorting is charge-based.

22. The method of claim 16, wherein greater resolution of said biopolymers is achieved when said applied voltage is greater than 40 V.

23. The method of claim 16, wherein said depth of said vertical gaps are from about 0.1-10 µm.

24. The method of claim 16, wherein said obstacles in said rows are laterally shifted with respect to each row.

25. The method of claim 16, wherein said sample inlet is a microchannel, in fluid communication with said channels.

26. The method of claim 16, wherein said microfluidic channels are in fluid communication with a reservoir.

27. The method of claim 26, wherein voltage is applied to said reservoir.

28. The method of claim 26, wherein said applied voltage is less than 1000 V.

29. The method of claim 28, wherein pressure is applied to said reservoir.

30. The method of claim 16, wherein said electrostatic force field or hydrodynamic force field is applied in pulse-field operation mode.

31. The method of claim 16, wherein said electrostatic force field or hydrodynamic force field is applied in continuous-field operation mode.

32. The method of claim 16, wherein said fluid mixture comprises a cell lysate or tissue homogenate.

33. The method of claim 16, wherein said fluid mixture comprises a large sample of deoxyribonucleic acids (DNA), proteins, or a combination thereof.

34. The method of claim 16, wherein said fluid mixture comprises a buffered solution.

35. The method of claim 34, further comprising the step of sorting a sample of said mixture two or more times, wherein the pH or ionic strength of said buffered solution is varied at the time of said sorting.

* * * * *